United States Patent [19]

Lee et al.

[11] Patent Number: 5,750,531
[45] Date of Patent: May 12, 1998

[54] PYRIMIDINE DERIVATIVES AND PROCESSES FOR THE PREPARATION THEREOF

[75] Inventors: Jong Wook Lee, Kwacheon-Si; Jeong Seok Chae, Seoul; Chang Seop Kim, Ansan-Si; Jae Kyu Kim, Kwacheon-Si; Dae Sung Lim, Seoul; Moon Kyu Shon, Anyang-Si; Yeon Shik Choi, Suwon-Si; Sang Ho Lee, Masan-Si, all of Rep. of Korea

[73] Assignee: Yuhan Corporation, Seoul, Rep. of Korea

[21] Appl. No.: 776,220

[22] PCT Filed: Aug. 10, 1995

[86] PCT No.: PCT/KR95/00105

§ 371 Date: Jan. 23, 1997

§ 102(e) Date: Jan. 23, 1997

[87] PCT Pub. No.: WO96/05177

PCT Pub. Date: Feb. 22, 1996

[30] Foreign Application Priority Data

Aug. 13, 1994 [KR] Rep. of Korea ............... 94-19997
Aug. 13, 1994 [KR] Rep. of Korea ............... 94-19998

[51] Int. Cl.$^6$ ............... A61K 31/505; C07D 239/02; C07D 239/70
[52] U.S. Cl. ............... 514/256; 514/258; 514/275; 544/253; 544/297; 544/326; 544/328; 544/334
[58] Field of Search ............... 514/256, 258, 514/275; 544/253, 297, 326, 328, 334

[56] References Cited

FOREIGN PATENT DOCUMENTS

WO 92/07844  5/1992  WIPO.
WO 94/14795  7/1994  WIPO.

*Primary Examiner*—Mukund J. Shah
*Assistant Examiner*—Brenda Coleman
*Attorney, Agent, or Firm*—Anderson, Kill & Olick, P.C.

[57] ABSTRACT

The present invention relates to novel pyrimidine derivatives of the formulae (I-1) and (I-2) and pharmaceutically acceptable salts thereof which possess an excellent anti-secretory activity, pharmaceutical compositions containing same as an active ingredient, their novel intermediates, and processes for the preparation thereof:

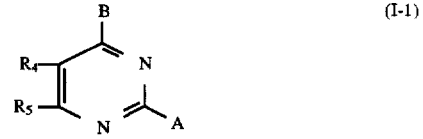

(I-1)

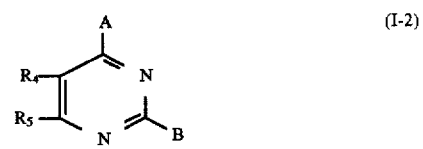

(I-2)

wherein:

$R_4$ and $R_5$, which may be the same or different, are independently hydrogen or a $C_1$–$C_3$ alkyl group, or jointly form a cyclopentyl or cyclohexyl ring;

A is a group of formula(II):

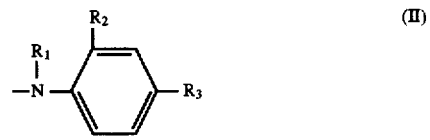

(II)

wherein $R_1$ and $R_2$ are, independently of each other, hydrogen or a $C_1$–$C_3$ alkyl group, and $R_3$ is hydrogen, a $C_1$–$C_3$ alkyl group or a halogen; and B is 1-(substituted)-1,2,3,4-tetrahydroisoquinolin-2-yl of formula (III-1) or 7-(substituted)-4,5,6,7-tetrahydrothieno[2,3-c]pyridin-6-yl of formula (III-2)

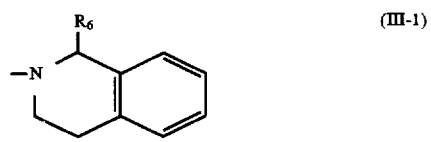

(III-1)

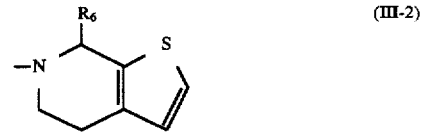

(III-2)

wherein $R_6$ is hydrogen or a $C_1$–$C_3$ alkyl group.

13 Claims, No Drawings

PYRIMIDINE DERIVATIVES AND PROCESSES FOR THE PREPARATION THEREOF

This application is a 371 of PCT/KR95/00105 filed Aug. 10, 1995.

FIELD OF THE INVENTION

The present invention relates to novel pyrimidine derivatives and pharmaceutically acceptable salts thereof which possess an excellent anti-secretory activity, pharmaceutical compositions containing same as an active ingredient, their novel intermediates, and processes for the preparation thereof.

BACKGROUND OF THE INVENTION

For the treatment of peptic ulcer disease, various drugs such as antacid, anticholinergic agent, $H_2$-receptor antagonist and proton pump inhibitor have been used. Recently, the advent of omeprazole useful as a proton pump inhibitor has rekindled research activities in this field.

However, it has been pointed out that the proton pump inhibition by omeprazole is irreversible, which may induce side effects. Accordingly, various attempts to develop a reversible proton pump inhibitor are being actively made. For example, European Patent Nos. 322133 and 404322 disclose quinazoline derivatives, European Patent No. 259174 describes quinoline derivatives, and WO 91/13337 offers pyrimidine derivatives, as a reversible proton pump inhibitor. Further, the present inventors have also reported quinazoline derivatives in WO 94/14795.

SUMMARY OF THE INVENTION

The present inventors have carried out extensive research to develop a reversible proton pump inhibitor with improved efficacy; and, as a result, have discovered that pyrimidine derivatives having a tetrahydroisoquinoline group at the 2- or 4-position of the pyrimidine nucleus exhibit excellent proton pump inhibition effects and possess the ability to attain a reversible proton pump inhibition.

Accordingly, it is a primary object of the present invention to provide novel pyrimidine derivatives having a tetrahydroisoquinoline group at the 2- or 4-position of the pyrimidine nucleus, and pharmaceutically acceptable salts thereof.

It is another object of the present invention to provide processes for preparing said compounds.

It is a further object of the present invention to provide pharmaceutical compositions containing same as active ingredients.

It is still another object of the invention to provide novel intermediate compounds useful for the preparation of the novel pyrimidine derivatives.

DETAILED DESCRIPTION OF THE INVENTION

In accordance with the present invention, there are provided novel pyrimidine derivative compounds of formulae (I-1) and (I-2) inclusive of pharmaceutically acceptable salts thereof:

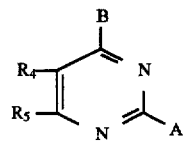

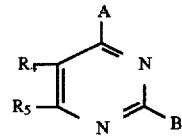

wherein:

$R_4$ and $R_5$, which may be the same or different, are independently hydrogen or a $C_1$–$C_3$ alkyl group, or jointly form a cyclopentyl or cyclohexyl ring;

A is a group of formula(II):

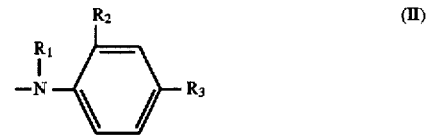

wherein $R_1$ and $R_2$ are, independently of each other, hydrogen or a $C_1$–$C_3$ alkyl group, and $R_3$ is hydrogen, a $C_1$–$C_3$ alkyl group or a halogen; and B is 1-(substituted)-1,2,3,4-tetrahydroisoquinolin-2-yl of formula (III-1) or 7-(substituted)-4,5,6,7-tetrahydrothieno[2,3-c]pyridin-6-yl of formula (III-2)

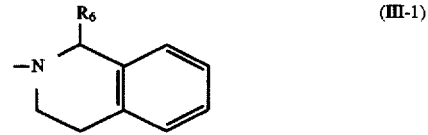

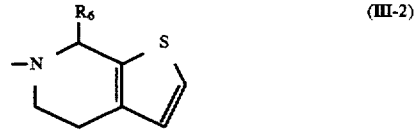

wherein $R_6$ is hydrogen or a $C_1$–$C_3$ alkyl group.

Among the compounds of the present invention, preferred are those wherein: $R_1$, $R_2$ and $R_6$ are independently hydrogen or a methyl group; $R_3$ is hydrogen or a fluorine; and $R_4$ and $R_5$, which may be the same or different, are independently hydrogen or a $C_1$–$C_3$ alkyl group, or jointly form a cyclopentyl or cyclohexyl ring.

Particularly, preferred compounds of the present invention are:

2-(2-methyl-4-fluorophenylamino)-4-(1-methyl-1,2,3,4-tetrahydroisoquinolin-2-yl)pyrimidine hydrochloride;

6-methyl-2-(2-methyl-4-fluorophenylamino)-4-(1-methyl-1,2,3,4-tetrahydroisoquinolin-2-yl)pyrimidine hydrochloride;

6-methyl-4-(1-methyl-1,2,3,4-tetrahydroisoquinolin-2-yl)-2-(4-fluorophenylamino)pyrimidine hydrochloride;

6-methyl-2-(N-methylphenylamino)-4-(1-methyl-1,2,3,4-tetrahydroisoquinolin-2-yl)pyrimidine hydrochloride;

6-ethyl-2-(2-methyl-4-fluorophenylamino)-4-(1-methyl-1,2,3,4-tetrahydroisoquinolin-2-yl)pyrimidine hydrochloride;

6-ethyl-2-(4-fluorophenylamino)-4-(1-methyl-1,2,3,4-tetrahydroisoquinolin-2-yl)pyrimidine hydrochloride;

6-ethyl-2-(N-methylphenylamino)-4-(1-methyl-1,2,3,4-tetrahydroisoquinolin-2-yl)pyrimidine hydrochloride;

6-ethyl-2-(2-methylphenylamino)-4-(1-methyl-1,2,3,4-tetrahydroisoquinolin-2-yl)pyrimidine hydrochloride;

2-(2-methyl-4-fluorophenylamino)-4-(1-methyl-1,2,3,4-tetrahydroisoquinolin-2-yl)-6-propylpyrimidine hydrochloride;

4-(1-methyl-1,2,3,4-tetrahydroisoquinolin-2-yl)-6-propyl-2-(4-fluorophenylamino)pyrimidine hydrochloride;

2-(N-methylphenylamino)-4-(1-methyl-1,2,3,4-tetrahydroisoquinolin-2-yl)-6-propylpyrimidine hydrochloride;

5,6-dimethyl-2-(2-methyl-4-fluorophenylamino)-4-(1-methyl-1,2,3,4-tetrahydroisoquinolin-2-yl)pyrimidine hydrochloride;

(R)-5,6-dimethyl-2-(2-methyl-4-fluorophenylamino)-4-(1-methyl-1,2,3,4-tetrahydroisoquinolin-2-yl)pyrimidine hydrochloride;

(S)-5,6-dimethyl-2-(2-methyl-4-fluorophenylamino)-4-(1-methyl-1,2,3,4-tetrahydroisoquinolin-2-yl)pyrimidine hydrochloride;

5,6-dimethyl-2-(4-fluorophenylamino)-4-(1-methyl-1,2,3,4-tetrahydroisoquinolin-2-yl)pyrimidine hydrochloride;

(R)-5,6-dimethyl-2-(4-fluorophenylamino)-4-(1-methyl-1,2,3,4-tetrahydroisoquinolin-2-yl)pyrimidine hydrochloride;

(S)-5,6-dimethyl-2-(4-fluorophenylamino)-4-(1-methyl-1,2,3,4-tetrahydroisoquinolin-2-yl)pyrimidine hydrochloride;

5,6-dimethyl-2-(N-methylphenylamino)-4-(1-methyl-1,2,3,4-tetrahydroisoquinolin-2-yl)pyrimidine hydrochloride;

(R)-5,6-dimethyl-2-(N-methylphenylamino)-4-(1-methyl-1,2,3,4-tetrahydroisoquinolin-2-yl)pyrimidine hydrochloride;

(S)-5,6-dimethyl-2-(N-methylphenylamino)-4-(1-methyl-1,2,3,4-tetrahydroisoquinolin-2-yl)pyrimidine hydrochloride;

5,6-dimethyl-2-(phenylamino)-4-(1-methyl-1,2,3,4-tetrahydroisoquinolin-2-yl)pyrimidine hydrochloride;

(R)-5,6-dimethyl-2-(4-phenylamino)-4-(1-methyl-1,2,3,4-tetrahydroisoquinolin-2-yl)pyrimidine hydrochloride;

(S)-5,6-dimethyl-2-(4-fluorophenylamino)-4-(1-methyl-1,2,3,4-tetrahydroisoquinolin-2-yl)pyrimidine hydrochloride;

5,6-dimethyl-2-(2-methylphenylamino)-4-(1-methyl-1,2,3,4-tetrahydroisoquinolin-2-yl)pyrimidine hydrochloride;

5,6-dimethyl-2-(4-methylphenylamino)-4-(1-methyl-1,2,3,4-tetrahydroisoquinolin-2-yl)pyrimidine hydrochloride;

5-methyl-6-ethyl-2-(2-methyl-4-fluorophenylamino)-4-(1-methyl-1,2,3,4-tetrahydroisoquinolin-2-yl)pyrimidine hydrochloride;

5-methyl-6-ethyl-2-(4-fluorophenylamino)-4-(1-methyl-1,2,3,4-tetrahydroisoquinolin-2-yl)pyrimidine hydrochloride;

5-methyl-6-ethyl-2-(N-methylphenylamino)-4-(1-methyl-1,2,3,4-tetrahydroisoquinolin-2-yl)pyrimidine hydrochloride;

2-(2-methyl-4-fluorophenylamino)-4-(1-methyl-1,2,3,4-tetrahydroisoquinolin-2-yl)cyclopenta[d]pyrimidine hydrochloride;

2-(4-fluorophenylamino)-4-(1-methyl-1,2,3,4-tetrahydroisoquinolin-2-yl)cyclopenta[d]pyrimidine hydrochloride;

2-(N-methylphenylamino)-4-(1-methyl-1,2,3,4-tetrahydroisoquinolin-2-yl)cyclopenta[d]pyrimidine hydrochloride;

2-(2-methyl-4-fluorophenylamino)-4-(1-methyl-1,2,3,4-tetrahydroisoquinolin-2-yl)-5,6,7,8-tetrahydroquinazoline hydrochloride;

2-(N-methylphenylamino)-4-(1-methyl-1,2,3,4-tetrahydroisoquinoline-2-yl)-5,6,7,8-tetrahydroquinazoline hydrochloride;

6-methyl-2-(2-methyl-4-fluorophenylamino)-4-(1,2,3,4-tetrahydroisoquinolin-2-yl)pyrimidine hydrochloride;

6-methyl-2-(4-fluorophenylamino)-4-(1,2,3,4-tetrahydroisoquinoline-2-yl)pyrimidine hydrochloride;

6-methyl-2-(N-methylphenylamino)-4-(1,2,3,4-tetrahydroisoquinolin-2-yl)pyrimidine hydrochloride;

6-ethyl-2-(2-methyl-4-fluorophenylamino)-4-(1,2,3,4-tetrahydroisoquinolin-2-yl)pyrimidine hydrochloride;

6-ethyl-2-(4-fluorophenylamino)-4-(1,2,3,4-tetrahydroisoquinolin-2-yl)pyrimidine hydrochloride;

6-ethyl-2-(N-methylphenylamino)-4-(1,2,3,4-tetrahydroisoquinolin-2-yl)pyrimidine hydrochloride;

6-ethyl-2-(2-methylphenylamino)-4-(1,2,3,4-tetrahydroisoquinolin-2-yl)pyrimidine hydrochloride;

5,6-dimethyl-2-(2-methyl-4-fluorophenylamino)-4-(1,2,3,4-tetrahydroisoquinolin-2-yl)pyrimidine hydrochloride;

5,6-dimethyl-2-(4-fluorophenylamino)-4-(1,2,3,4-tetrahydroisoquinolin-2-yl)pyrimidine hydrochloride;

5,6-dimethyl-2-(N-methylphenylamino)-4-(1,2,3,4-tetrahydroisoquinolin-2-yl)pyrimidine hydrochloride;

5-methyl-6-ethyl-2-(2-methyl-4-fluorophenylamino)-4-(1,2,3,4-tetrahydroisoquinolin-2-yl)pyrimidine hydrochloride;

5-methyl-6-ethyl-2-(4-fluorophenylamino)-4-(1,2,3,4-tetrahydroisoquinolin-2-yl)pyrimidine hydrochloride;

5-methyl-6-ethyl-2-(N-methylphenylamino)-4-(1,2,3,4-tetrahydroisoquinolin-2-yl)pyrimidine hydrochloride;

2-(2-methyl-4-fluorophenylamino)-4-(1,2,3,4-tetrahydroisoquinolin-2-yl)cyclopenta[d]pyrimidine hydrochloride;

2-(2-methyl-4-fluorophenylamino)-4-(1,2,3,4-tetrahydroisoquinolin-2-yl)-5,6,7,8-tetrahydroquinazolinehydrochloride;

2-(4-fluorophenylamino)-4-(1,2,3,4-tetrahydroisoquinolin-2-yl)-5,6,7,8-tetrahydroquinazoline hydrochloride;

2-(N-methylphenylamino)-4-(1,2,3,4-tetrahydroisoquinolin-2-yl)-5,6,7,8-tetrahydroquinazoline hydrochloride;

2-(2-methylphenylamino)-4-(1,2,3,4-tetrahydroisoquinolin-2-yl)-5,6,7,8-tetrahydroquinazoline hydrochloride;

6-methyl-2-(2-methyl-4-fluorophenylamino)-4-(7-methyl-4,5,6,7-tetrahydrothieno[2,3-c]pyridin-6-yl)pyrimidine hydrochloride;

6-methyl-4-(7-methyl-4,5,6,7-tetrahydrothieno[2,3-c]pyridin-6-yl)-2-(4-fluorophenylamino)pyrimidine hydrochloride;

6-methyl-2-(N-methylphenylamino)-4-(7-methyl-4,5,6,7-tetrahydrothieno[2,3-c]pyridin-6-yl)pyrimidine hydrochloride;

5,6-dimethyl-2-(2-methyl-4-fluorophenylamino)-4-(7-methyl-4,5,6,7-tetrahydrothieno[2,3-c]pyridin-6-yl)pyrimidine hydrochloride;

5-methyl-2-(2-methyl-4-fluorophenylamino)-4-(7-methyl-4,5,6,7-tetrahydrothieno[2,3-c]pyridin-6-yl)-6-ethylpyrimidine hydrochloride;

6-methyl-4-(2-methyl-4-fluorophenylamino)-2-(1-methyl-1,2,3,4-tetrahydroisoquinolin-2-yl)pyrimidine hydrochloride;

6-methyl-4-(4-fluorophenylamino)-2-(1-methyl-1,2,3,4-tetrahydroisoquinolin-2-yl)pyrimidine hydrochloride;

6-methyl-4-(2-methyl-4-fluorophenylamino)-2-(7-methyl-4,5,6,7-tetrahydrothieno[2,3-c]pyridin-6-yl)pyrimidine hydrochloride;

6-methyl-4-(4-fluorophenylamino)-2-(7-methyl-4,5,6,7-tetrahydrothieno[2,3-c]pyridin-6-yl)pyrimidine hydrochloride;

6-ethyl-2-(2-methyl-4-fluorophenylamino)-4-(1-methyl-1,2,3,4-tetrahydroisoquinolin-2-yl)pyrimidine hydrochloride;

6-ethyl-4-(2-methyl-4-fluorophenylamino)-2-(1,2,3,4-tetrahydroisoquinolin-2-yl)pyrimidine hydrochloride;

6-ethyl-4-(4-fluorophenylamino)-2-(1,2,3,4-tetrahydroisoquinolin-2-yl)pyrimidine hydrochloride;

6-ethyl-4-(N-methylphenylamino)-2-(1,2,3,4-tetrahydroisoquinolin-2-yl)pyrimidine hydrochloride;

5,6-dimethyl-4-(2-methyl-4-fluorophenylamino)-2-(1-methyl-1,2,3,4-tetrahydroisoquinolin-2-yl)pyrimidine hydrochloride;

(R)-5,6-dimethyl-4-(2-methyl-4-fluorophenylamino)-2-(1-methyl-1,2,3,4-tetrahydroisoquinolin-2-yl)pyrimidine hydrochloride;

(S)-5,6-dimethyl-4-(2-methyl-4-fluorophenylamino)-2-(1-methyl-1,2,3,4-tetrahydroisoquinolin-2-yl)pyrimidine hydrochloride;

5,6-dimethyl-4-(4-fluorophenylamino)-2-(1-methyl-1,2,3,4-tetrahydroisoquinolin-2-yl)pyrimidine hydrochloride;

(R)-5,6-dimethyl-4-(4-fluorophenylamino)-2-(1-methyl-1,2,3,4-tetrahydroisoquinolin-2-yl)pyrimidine hydrochloride;

(S)-5,6-dimethyl-4-(4-fluorophenylamino)-2-(1-methyl-1,2,3,4-tetrahydroisoquinolin-2-yl)pyrimidine hydrochloride;

5,6-dimethyl-4-(N-methylphenylamino)-2-(1-methyl-1,2,3,4-tetrahydroisoquinolin-2-yl)pyrimidine hydrochloride;

(R)-5,6-dimethyl-4-(N-methylphenylamino)-2-(1-methyl-1,2,3,4-tetrahydroisoquinolin-2-yl)pyrimidine hydrochloride;

(S)-5,6-dimethyl-4-(N-methylphenylamino)-2-(1-methyl-1,2,3,4-tetrahydroisoquinolin-2-yl)pyrimidine hydrochloride;

5,6-dimethyl-4-(2-methyl-4-fluorophenylamino)-2-(1,2,3,4-tetrahydroisoquinolin-2-yl)pyrimidine hydrochloride;

5,6-dimethyl-4-(4-fluorophenylamino)-2-(1,2,3,4-tetrahydroisoquinolin-2-yl)pyrimidine hydrochloride;

5,6-dimethyl-4-(N-methylphenylamino)-2-(1,2,3,4-tetrahydroisoquinolin-2-yl)pyrimidine hydrochloride;

5,6-dimethyl-4-(2-methyl-4-fluorophenylamino)-2-(7-methyl-4,5,6,7-tetrahydrothieno[2,3-c]pyridin-6-yl)pyrimidine hydrochloride;

5,6-dimethyl-2-(7-methyl-4,5,6,7-tetrahydrothieno[2,3-c]pyridin-6-yl)-4-(4-fluorophenylamino)pyrimidine hydrochloride;

5,6-dimethyl-4-(N-methylphenylamino)-2-(7-methyl-4,5,6,7-tetrahydrothieno[2,3-c]pyridin-6-yl)pyrimidine hydrochloride;

5-methyl-6-ethyl-4-(2-methyl-4-fluorophenylamino)-2-(1-methyl-1,2,3,4-tetrahydroisoquinolin-2-yl)pyrimidine hydrochloride;

4-(2-methyl-4-fluorophenylamino)-2-(1-methyl-1,2,3,4-tetrahydroisoquinolin-2-yl)cyclopenta[d]pyrimidine hydrochloride;

2-(2-methyl-4-fluorophenylamino)-4-(1-methyl-1,2,3,4-tetrahydroisoquinolin-2-yl)-5,6,7,8-tetrahydroquinazoline hydrochloride; and 4-(2-methyl-4-fluorophenylamino)-2-(1,2,3,4-tetrahydroisoquinolin-2-yl)-5,6,7,8-tetrahydroquinazoline hydrochloride.

The pyrimidine derivatives of formulae (I-1) and (I-2) in the present invention may exist in the form of an optical isomer, (R) or (S), or a mixture thereof. Both types of the isomeric compounds are found to exhibit excellent antisecretory activity.

The compounds of formulae (I-1) and (I-2) may be prepared in accordance with Scheme 1 and Scheme 2, respectively, described below.

Scheme 1

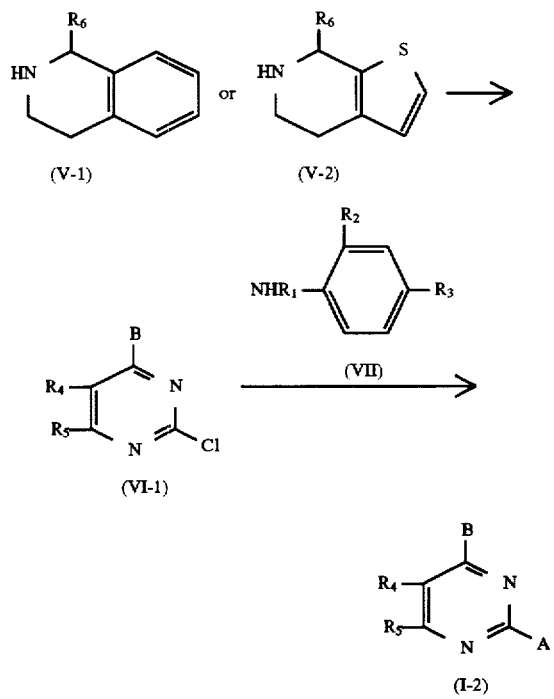

wherein A, B, R$_1$, R$_2$, R$_3$, R$_4$, R$_5$ and R$_6$ are the same as defined as above.

Specifically, the compound of formula (I-1) may be prepared by a process which comprises: reacting a compound of formula (IV) with a compound of formula (V-1) or (V-2) to give a compound of formula (VI-1); and reacting the compound of formula (VI-1) with a compound of formula (VII).

Scheme 2

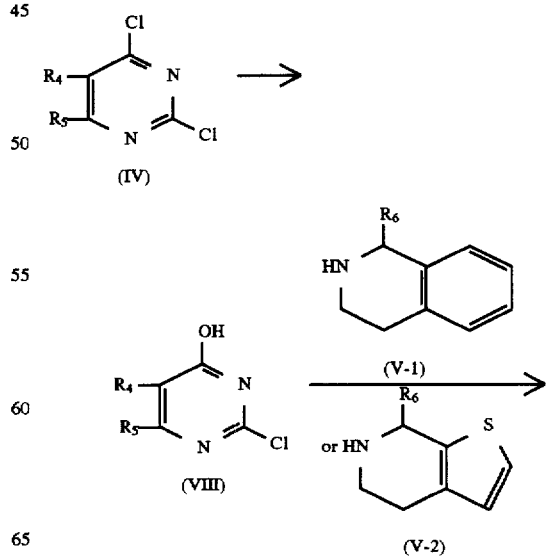

-continued
Scheme 2

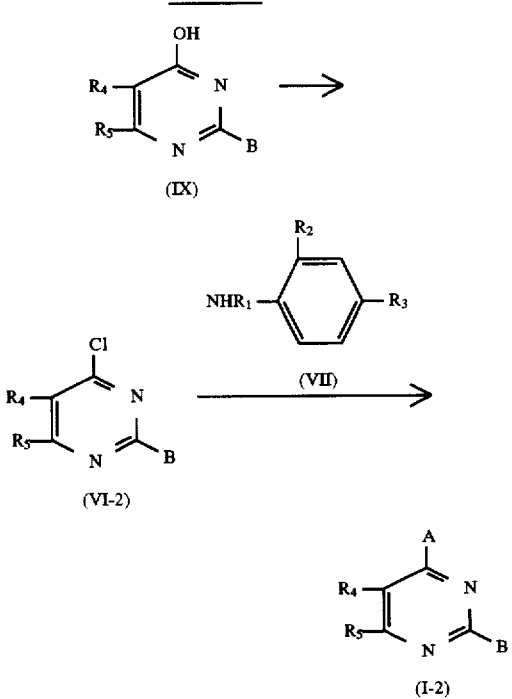

wherein A, B, R₁, R₂, R₃, R₄, R₅ and R₆ are the same as defined as above.

Further, the compound of formula(I-2) may be prepared by a process which comprises: hydrolyzing a compound of formula(IV) at its 4-position to give a compound of formula (VIII); reacting the compound of formula(VIII) with a compound of formula (V-1) or (V-2) to give a compound of formula(IX); chlorinating the compound of formula(IX) at its 4-position to give a compound of formula (VI-2); and then reacting the compound of formula (VI-2) with a compound of formula (VII).

In the processes of Scheme 1 and Scheme 2, the compound of formula(IV) may be prepared by using a known process [see, e.g., *J. Heterocyclic Chem.*, 28, 231(1991); and *Org. Synth., Coll. Vol.* 638], and the compounds of formula (V-1) and (V-2) may be prepared in accordance with the process disclosed in European Patent No. 230871. The compound of formula(VII) is commercially available(for example from Aldrich Co. in U.S.A.)

As shown in Scheme 1 and Scheme 2, the pyrimidine compounds (IV) and (VIII) are reacted with the compounds of formula (V-1) or (V-2) in the presence of an appropriate solvent and a base for 1 to 24 hours to give the compounds of formula (VI-1) or (VI-2), respectively. Suitable solvents for this reaction may include dichloromethane, acetone, acetonitrile and dimethylformamide. The reaction temperature preferably ranges from a room temperature to 150° C. Suitable bases for this reaction may include triethylamine, N,N-dimethylaniline and pyridine.

The substituted pyrimidine compounds of formula(VI-1) and (VI-2) so obtained are then reacted with the compounds of formula(VII) in an appropriate solvent for 2 to 5 hours to give the present compounds of formula (I-1) and (I-2), respectively. Suitable solvents for this reaction may include dimethylformamide, p-dioxane, dimethylsulfoxide and the like. The reaction temperature preferably ranges from 80° C. and 140° C.

In the process of Scheme 2, prior to the reaction with the compound of formula (V-1) or (V-2), the 4-position of the compound of formula (IV) may be hydrolyzed selectively using NaOH solution in an appropriate solvent. Suitable solvents for this reaction may include acetone, acetonitrile and tetrahydrofurane.

The compound of formula (VI-2) is prepared from the compound of formula(IX) by using a chlorinating agent such as phosphorous oxychloride.

The compounds of formula (VI-1) and (VI-2) prepared as above are novel and useful as intermediates for the preparation of the pyrimidine compounds of formula(I-1) or (I-2). Therefore, the present invention encompasses, within its scope, the novel compounds of formula (VI-1) or (VI-2) and processes for the preparation thereof.

The compounds of the present invention may be administered, either orally or intraperitoneally, in an effective amount ranging from 0.1 to 500 mg/kg, preferably from 1.0 to 100 mg/kg into a subject patient per day.

The present invention further includes, within its scope, pharmaceutically acceptable salts of the compounds of formula(I-1) and (I-2). The non-toxic salts which fall within the scope of the present invention may include inorganic acid salts such as hydrochloride, sulfate, phosphate and nitrate, and organic acid salts such as tartrate, fumarate, citrate, mesylate and acetate.

The pharmaceutically acceptable salts may be prepared in accordance with a known method, e.g., by reacting the compounds of formula (I-1) or (I-2) with the acids mentioned above in the presence of a solvent, e.g., ethyl alcohol, dichloromethane, ethyl acetate and diethyl ether.

The present invention also includes within its scope pharmaceutical compositions comprising one or more of the inventive compounds as an active ingredient, in association with a pharmaceutically acceptable carrier, excipient and/or other additives, if necessary. The active ingredient present in the composition may range from 0.1% to 99.9% by weight thereof.

The following Examples are given for the purpose of illustration only, and are not intended to limit the scope of the invention. 1-Methyl-1,2,3,4-tetrahydroisoquinoline, (R)-1-methyl-1,2,3,4-tetrahydroisoquinoline and (S)-1-methyl-1,2,3,4-tetrahydroisoquinoline were prepared by the same method as described in Preparation of WO 94/14795.

PREPARATION 1

Preparation of 7-methyl-4,5,6,7-tetrahydrothieno[2,3-c]pyridine

Step 1: 2-(3-thienyl)chloroethane

Thionyl chloride(17 ml, 0.23 mol) was added dropwise to a mixture solution of 2-(3-thienyl)ethanol(22.4 ml, 0.2 mol) and chloroform(60 ml) while maintaining the temperature of the reaction system below 10° C., followed by stirring at room temperature for 1 hour. Then the reaction mixture was concentrated under a reduced pressure and distilled in vacuo to give 24 g of the titled compound. (Yield: 81.5%)

Step 2: 7-methyl-6,7-dihydrothieno[2,3-c]pyridine

To a solution of 2-(3-thienyl)chloroethane(20 g, 0.136 mol) prepared in the above Step 1 and anhydrous acetonitrile (350 ml) was added tin(IV) chloride(20 ml, 0.17 mol) at room temperature. The reaction mixture was heated to reflux for 16 hours and cooled, to which water was added to remove excess tin(IV) chloride. And then the reaction mixture was washed by dichloromethane. The water layer was separated and basified with aqueous K₂CO₃ solution under ice-cooling and then extracted with dichloromethane. The combined dichloromethane layers were dried over magnesium sulfate and concentrated to give 10.56 g of the titled compound. (Yield: 51%)

Step 3: 7-methyl-4,5,6,7-tetrahydrothieno[2,3-c]pyridine

Sodium borohydride(4.4 g, 116 mmol) was added portionwise at room temperature to a mixture solution of 7-methyl-6,7-dihydrothieno[2,3-c]pyridine(10.5 g, 69.4 mmol) prepared in the above Step 2 and ethanol(100 ml). After stirring for 1 hour, the reaction mixture was diluted with water, and extracted with dichloromethane. The combined dichloromethane layers were dried over magnesium sulfate and concentrated to give 10.34 g of the titled compound. (Yield: 97%)

PREPARATION 2

Preparation of 2,4-dichloro-6-ethylpyrimidine

Step 1: 2-mercapto-6-ethylpyrimidine-4-one

To a solution of sodium methoxide(24 g, 0.44 mol) and ethanol(180 ml) were added thiourea(15.22 g, 0.2 mol) and methyl propionylacetate(25.1 ml, 0.2 mol). After distillating solvent slowly, water(200 ml) was added to the reaction mixture, which was then heated to reflux for 30 minutes. Active carbon was added to the reaction mixture, which was then stirred for 5 minutes and filtered. The filtrate was cooled to a room temperature and acidified by glacial acetic acid and the resulting solid was filtered and dried to give 29 g of the titled compound. (Yield: 93%)

Step 2: 2,4-dihydroxy-6-ethylpyrimidine

A mixture solution of chloroacetic acid(33.3 g, 0.352 mol), water(400 ml) and 2-mercapto-6-ethylpyrimidine-4-one(29 g, 0.186 mol) prepared in the above Step 1 was heated to reflux for 14 hours and cooled to a room temperature. To the reaction mixture was added conc. HCl(95 ml) and the mixture was heated to reflux for 1 day. After the reaction mixture was cooled to a room temperature and concentrated under a reduced pressure, the residue was diluted with water. After stirring for 2 hours, the resulting solid was filtered and dried to give 11.16 g of the titled compound. (Yield: 43%)

Step 3: 2,4-dichloro-6-ethylpyrimidine

A mixture of phosphorous oxychloride(43 ml), N,N-dimethyl aniline(6.6 ml) and 2,4-dihydroxy-6-ethyl pyrimidine(11.12 g, 79.3 mmol) prepared in the above Step 2 was heated to reflux for 6 hours. The reaction mixture was cooled to a room temperature and diluted with dichloromethane. The diluted solution was added slowly to ice water, while maintaining the temperature of the reaction system below 10° C. and the mixture was extracted with dichloromethane. The combined dichloromethane layers were dried over magnesium sulfate and concentrated to give 13.10 g of the titled compound as an oily form. (Yield: 93.3%)

PREPARATION 3

Preparation of 2,4-dichloro-6-propylpyrimidine

In accordance with the same procedure as in Preparation 2, except that sodium methoxide(24 g, 0.44 mol), thiourea (15.22 g, 0.2 mol), ethyl butyrylacetate(31.6 ml, 0.2 mol) and ethanol(180 ml) were used as starting materials, 10.5 g of the titled compound was prepared as an oily form.

PREPARATION 4

Preparation of 2,4-dichloro-5-methyl-6-ethylpyrimidine

In accordance with the same procedure as in Preparation 2, except that sodium methoxide(24 g, 0.44 mol), thiourea (15.22 g, 0.2 mol), ethyl 2-propionyl propionate(31.6 g, 0.2 mol) and ethanol(180 ml) were used as starting materials, 16.5 g of the title compound was prepared as an oily form.

EXAMPLE 1

Synthesis of 2-(2-methyl-4-fluorophenylamino)-4-(1-methyl-1,2,3,4-tetrahydroisoquinolin-2-yl) pyrimidine hydrochloride Step 1: 4-(1-Methyl-1,2,3,4-tetrahydroisoquinolin-2-yl)-2-chloropyrimidine A mixture solution of 2,4-dichloropyrimidine(3.0 g, 20 mmol), 1-methyl-1,2,3,4-tetrahydroisoquinoline(3.3 g, 22 mmol), triethylamine(3.4 ml, 24.4 mmol) and N,N-dimethyl formamide(20 ml) was stirred for 5 hours, diluted with dichloromethane, washed with water several times. The dichloromethane layer was separated, dried over anhydrous sodium sulfate and then concentrated under a reduced pressure. The resulting residue was crystallized by silica gel column chromatography to give 1.5 g of the titled compound. (Yield: 28.9%)

Step 2: 2-(2-Methyl-4-fluorophenylamino)-4-(1-methyl-1,2,3,4-tetrahydroisoquinolin-2-yl)pyrimidine hydrochloride 2-Methyl-4-fluoroaniline(1.1 ml, 10.2 mmol) was added to a mixture solution of 4-(1-methyl-1,2,3,4-tetrahydroisoquinolin-2-yl)-2-chloropyrimidine(1.5 g, 5.8 mmol) and dimethylformamide(10 ml). The reaction mixture was stirred for 3 hours at 110°–120° C., cooled to a room temperature, diluted with dichloromethane, and then washed with water. The dichloromethane layer was separated, basified with aqueous sodium hydroxide, washed with water, dried and concentrated. The resulting residue was crystallized by silica gel column chromatography to give free base form of the titled compound. To a mixture solution of the free base form of the titled compound and ethyl ether was added aqueous hydrochloric acid and the resulting titled compound was filtered and dried in vacuo. Recrystallization from ethanol afforded 1.2 g of the titled compound as a white crystalline solid.

Yield: 58.6%

M.P.: 160°–163° C.

$^1$H-NMR(DMSO-d$_6$): δ 1.49(d, 3H), 2.30(s, 3H), 2.90(m, 2H), 3.45(m, 1H), 4.20(bs, 1H), 5.40(bs, 1H), 6.05(d, 1H), 6.45(s, 1H), 6.90(m, 2H), 7.18(m, 4H), 7.88(m, 4H), 7.95(d, 1H).

EXAMPLE 2

Synthesis of 6-methyl-2-(2-methyl-4-fluorophenylamino)-4-(1-methyl-1,2,3,4-tetrahydroisoquinolin-2-yl)pyrimidine hydrochloride Step 1: 6-methyl-4-(1-methyl-1,2,3,4-tetrahydroisoquinolin-2-yl)-2-chloropyrimidine In accordance with the same procedure as in Step 1 of Example 1, except that 6-methyl-2,4-dichloropyrimidine (6.52 g, 40 mmol), 1-methyl-1,2,3,4-tetrahydroisoquinoline (6.6 g, 44 mmol), triethylamine(6.8 ml, 48.8 mmol) and N,N-dimethylformamide(30 ml) were used as starting materials, 5.5 g of the titled compound was prepared. (Yield: 50.2%)

Step 2: 6-methyl-2-(2-methyl-4-fluorophenylamino)-4-(1-methyl-1,2,3,4-tetrahydroisoquinolin-2-yl)pyrimidine hydrochloride After 2-methyl-4-fluoroaniline(1.1 ml, 10.2 mmol) was added to a mixture solution of 6-methyl-4-(1-methyl-1,2,3,4-tetrahydroisoquinolin-2-yl)-2-chloropyrimidine(1.5 g, 5.5 mmol) and dimethylformamide(10 ml), 1.2 g of the titled compound was obtained in accordance with the same procedure as in Step 2 of Example 1.

Yield: 51.7%
M.P.: 177°–179° C.
$^1$H-NMR(DMSO-d$_6$): δ 1.42(d, 3H), 2.30(s, 3H), 2.32(s, 3H), 2.90(m, 2H), 3.50(qq, 1H), 4.22(qq, 1H), 5.42(qq, 1H), 6.70(s, 1H), 7.18(m, 6H), 7.63(m, 1H), 9.80(s, 1H), 13.30 (bs, 1H).

EXAMPLE 3

Synthesis of 6-methyl-4-(1-methyl-1,2,3,4-tetrahydroisoquinolin-2-yl)-2-(4-fluorophenylamino) pyrimidine hydrochloride After 4-fluoroaniline(0.8 ml, 8.4 mmol) was added to a mixture solution of 6-methyl-4-(1-methyl-1,2,3,4-tetrahydroisoquinolin-2-yl)-2-chloropyrimidine(1.5 g, 5.5 mmol) and dimethylformamide (10 ml), 1.5 g of the title compound was obtained in accordance with the same procedure as in Step 2 of Example 1.
Yield: 70.7%
M.P.: 194°–196° C.
$^1$H-NMR(DMSO-d$_6$): δ 1.50(d, 3H), 2.38(s, 3H), 2.92(bs, 2H), 3.50(m, 1H), 4.30(qq, 1H), 5.58(qq, 1H), 6.70(s, 1H), 7.1–7.40(m, 6H), 7.60(m, 2H), 10.50(s, 1H), 13.10(bs, 1H).

EXAMPLE 4

Synthesis of 6-methyl-2-(N-methylphenylamino)-4-(1-methyl-1,2,3,4-tetrahydroisoquinolin-2-yl) pyrimidine hydrochloride After N-methylaniline(0.9 ml, 8.4 mmol) was added to a mixture solution of 6-methyl-4-(1-methyl-1,2,3,4-tetrahydroisoquinolin-2-yl)-2-chloropyrimidine(1.5 g, 5.5 mmol) and dimethylformamide(10 ml), 1.2 g of the titled compound was obtained in accordance with the same procedure as in Step 2 of Example 1
Yield: 57.3%
M.P.: 170°–172° C.
$^1$H-NMR(DMSO-d$_6$): δ 1.40(d, 3H), 2.38(s, 3H), 2.95(m, 2H), 3.58(s, 3H), 3.60(bs, 1H), 4.30(qq, 1H), 5.50(qq, 1H), 6.70(s, 1H), 7.10–7.38(m, 4H), 7.40–7.60(m, 5H), 12.00(s, 1H).

EXAMPLE 5

Synthesis of 6-ethyl-2-(2-methyl-4-fluorophenylamino)-4-(1-methyl-1,2,3,4-tetrahydroisoquinolin-2-yl)pyrimidine hydrochloride
Step 1: 6-ethyl-4-(1-methyl-1,2,3,4-tetrahydroisoquinolin-2-yl)-2-chloropyrimidine
In accordance with the same procedure as in Step 1 of Example 1, except that 1-methyl-1,2,3,4-tetrahydroisoquinoline(4.1 g, 27.8 mmol), triethylamine(4.7 ml, 33.7 mmol), N,N-dimethylformamide(20 ml) and 6-ethyl-2,4-dichloropyrimidine(4.9 g, 27.7 mmol) obtained in Preparation 2 were used as starting materials, 5.58 g of the titled compound was prepared. (Yield: 70%)
Step 2: 6-ethyl-2-(2-methyl-4-fluorphenylamino)-4-(1-methyl-1,2,3,4-tetrahydroisoquinolin-2-yl)pyrimidine hydrochloride
After 2-methyl-4-fluoroaniline(0.77 ml, 6.93 mmol) was added to a mixture solution of 6-ethyl-4-(1-methyl-1,2,3,4-tetrahydroisoquinolin-2-yl)-2-chloropyrimidine(1.0 g, 3.47 mmol) and dimethylformamide(5 ml), 0.92 g of the titled compound was obtained in accordance with the same procedure as in Step 2 of Example 1.
Yield: 64%
M.P.: 172°–174° C.
$^1$H-NMR(CDCl$_3$): δ 1.38–1.60(tt+dd, 6H), 2.43(ss, 3H), 2.68–3.06(m, 4H), 3.76(m, 1H), 3.94(m, 1H), 5.33(qq, 1H), 6.01(ss, 1H), 6.85–7.30(m, 6H), 7.58(t, 1H), 9.83(s, 1H), 14.00(s, 1H).

EXAMPLE 6

Synthesis of 6-ethyl-2-(4-fluorophenylamino)-4-(1-methyl-1,2,3,4-tetrahydroisoquinolin-2-yl) pyrimidine hydrochloride After 4-fluoroaniline(0.38 ml, 4.01 mmol) was added to a mixture solution of 6-ethyl-4-(1-methyl-1,2,3,4-tetrahydroisoquinolin-2-yl)-2-chloropyrimidine (0.57 g, 1.98 mmol) and dimethylformamide (5 ml), 0.17 g of the titled compound was obtained in accordance with the same procedure as in Step 2 of Example 1
Yield: 22%
M.P.: 156°–158° C.
$^1$H-NMR(DMSO-d$_6$): δ 1.29(t, 3H), 1.49(d, 3H), 2.65(q, 2H), 2.93–2.96(m, 2H), 3.70(m, 1H), 4.05–4.60(m, 1H), 5.60(qq, 1H), 7.10–7.55(m, 6H), 7.60–7.65(m, 2H), 10.60(s, 1H), 10.90(s, 1H).

EXAMPLE 7

Synthesis of 6-ethyl-2-(N-methylphenylamino)-4-(1-methyl-1,2,3,4-tetrahydroisoquinolin-2-yl) pyrimidine hydrochloride After N-methylaniline(0.46 ml, 4.25 mmol) was added to a mixture solution of 6-ethyl-4-(1-methyl-1,2,3,4-tetrahydroisoquinolin-2-yl)-2-chloropyrimidine(0.61 g, 2.12 mmol) and dimethylformamide(5 ml), 0.50 g of the titled compound was obtained in accordance with the same procedure as in Step 2 of Example 1.
Yield: 60%
M.P.: 109°–111° C.
$^1$H-NMR(DMSO-d$_6$): δ 1.22(t, 3H), 1.43(dd, 3H), 2.78(q, 2H), 2.95(s, 1H), 3.30(m, 1H), 3.62(s, 3H), 4.37(mm, 1H), 5.70(q, 1H), 6.70(s, 1H), 7.06–7.58(m, 9H), 12.15(s, 1H).

EXAMPLE 8

Synthesis of 6-ethyl-2-(2-methylphenylamino)-4-(1-methyl-1,2,3,4-tetrahydroisoquinolin-2-yl) pyrimidine hydrochloride After 2-methylaniline(0.46 ml, 4.31 mmol) was added to a mixture solution of 6-ethyl-4-(1-methyl-1,2,3,4-tetrahydroisoquinolin-2-yl)-2-chloropyrimidine(0.61 g, 2.12 mmol) and dimethylformamide(5 ml), 0.52 g of the titled compound was obtained in accordance with the same procedure as in Step 2 of Example 1.
Yield: 62%
M.P.: 78°–81° C.
$^1$H-NMR(DMSO-d$_6$): δ 1.80–2.20(m, 6H), 2.90(s, 3H), 3.07 (s, 1H), 3.24(q, 2H), 3.43(s, 1H), 3.96(s, 3H), 4.16(mm, 1H), 4.88(mm, 1H), 6.08(qq, 1H), 7.23(ss, 1H), 7.64–7.90(m, 7H), 8.32(t, 1H), 10.50(s, 1H), 14.10(s, 1H).

EXAMPLE 9

Synthesis of 2-(2-methyl-4-fluorophenylamino)-4-(1-methyl-1,2,3,4-tetrahydroisoquinolin-2-yl)-6-propylpyrimidine hydrochloride
Step 1: 4-(1-methyl-1,2,3,4-tetrahydroisoquinolin-2-yl)-6-propyl-2-chloropyrimidine
In accordance with the same procedure as in Step 1 of Example 1, except that 1-methyl-1,2,3,4- tetrahydroisoquinoline(1.6 g, 10.9 mmol), triethylamine(1.6 ml, 11.5 mmol), N,N-dimethylformamide(20 ml) and 2,4-dichloro-6-propylpyrimidine(1.8 g, 9.4 mmol) obtained in Preparation 3 were used as starting materials, 1.6 g of the titled compound was prepared. (Yield: 56.4%)

Step 2: 2-(2-methyl-4-fluorophenylamino)-4-(1-methyl-1,2,3,4-tetrahydroisoquinolin-2-yl)-6-propylpyrimidine hydrochloride After 4-fluoro-2-methylaniline(0.35 ml, 3.15 mmol) was added to a mixture solution of 4-(1-methyl-1,2,3,4-tetrahydroisoquinolin-2-yl)-6-propyl-2-chloropyrimidine (0.5 g, 1.66 mmol) and dimethylformamide(5 ml), 0.2 g of the titled compound was obtained in accordance with the same procedure as in Step 2 of Example 1.
Yield: 28.2%
M.P.: 95°–97° C.
$^1$H-NMR(DMSO-d$_6$): δ 1.00(t, 3H), 1.50(dd, 3H), 1.81(q, 2H), 2.35(s, 3H), 2.70(t, 2H), 2.94(bd, 2H), 3.60(mm, 1H), 4.30(dd, 1H), 5.55(dd, 1H), 6.70(s, 1H), 7.22(bs, 6H), 7.75(bs, 1H), 9.90(s, 1H), 13.30(bs, 1H).

EXAMPLE 10

Synthesis of 4-(1-methyl-1,2,3,4-tetrahydroisoquinolin-2-yl)-6-propyl-2-(4-fluorophenylamino)pyrimidine hydrochloride After 4-fluoroaniline(0.27 ml, 2.85 mmol) was added to a mixture solution of 4-(1-methyl-1,2,3,4-tetrahydroisoquinolin-2-yl)-6-propyl-2-chloropyrimidine (0.5 g, 1.66 mmol) and dimethylformamide(5 ml), 0.3 g of the titled compound was obtained in accordance with the same procedure as in Step 2 of Example 1.
Yield: 43.8%
M.P.: 100°–105° C.
$^1$H-NMR(DMSO-d6): δ 0.96(t, 3H), 1.54(m, 3H), 1.75(q, 2H), 2.60(t, 2H), 2.96(m, 2H), 3.62(mm, 1H), 4.35(qq, 1H), 5.60(qq, 1H), 6.70(d, 1H), 7.00–7.40(m, 6H), 7.62(m, 2H).

EXAMPLE 11

2-(N-methylphenylamino)-4-(1-methyl-1,2,3,4-tetrahydroisoquinolin-2-yl)-6-propylpyrimidine hydrochloride After N-methylaniline(0.27 ml, 2.49 mmol) was added to a mixture solution of 4-(1-methyl-1,2,3,4-tetrahydroisoquinolin-2-yl)-6-propyl-2-chloropyrimidine (0.5 g, 1.66 mmol) and dimethylformamide (5 ml), 0.5 g of the title compound was obtained in accordance with the same procedure as in Step 2 of Example 1.
Yield: 73.6%
M.P.: 92°–94° C.
$^1$H-NMR(DMSO-d$_6$): δ 0.96(t, 3H), 1.46(dd, 3H), 1.59(q, 2H), 2.57(t, 2H), 2.90(bd, 2H), 3.50(mm+d, 4H), 4.35(qq, 1H), 5.56(qq, 1H), 6.65(d, 1H), 7.00–7.70(m, 9H).

EXAMPLE 12

Synthesis of 5,6-dimethyl-2-(2-methyl-4-fluorophenylamino)-4-(1-methyl-1,2,3,4-tetrahydroisoquinolin-2-yl)pyrimidine hydrochloride Step 1: 5,6-Dimethyl-2,4-dichloropyrimidine A mixture solution of 5,6-dimethyl-2,4-dihydroxy pyrimidine(72 g, 0.51 mol), phosphorus oxychloride(250 ml) and N,N-dimethylaniline(41 ml) was heated to reflux for 3 hours. After cooling to room temperature, the reaction mixture was added slowly to ice water. The resulting solid was filtered and recrystallized from dichloromethane to give 54.3 g of the titled compound. (Yield: 60%)

Step 2: 5,6-Dimethyl-4-(1-methyl-1,2,3,4-tetrahydroisoquinolin-2-yl)-2-chloropyrimidine In accordance with the same procedure as in Step 1 of Example 1, except that 1-methyl-1,2,3,4-tetrahydroisoquinoline(3.9 g, 26.4 mmol) and 5,6-dimethyl-2,4-dichloropyrimidine(4.3 g, 24 mmol) prepared in the above Step 1 were used as starting materials, 4.17 g of the titled compound was prepared. (Yield: 60.4%)

Step 3: 5,6-Dimethyl-2-(2-methyl-4-fluorophenylamino)-4-(1-methyl-1,2,3,4-tetrahydroisoquinolin-2-yl)pyrimidine hydrochloride After 2-methyl-4-fluoroaniline(1.1 ml, 9.9 mmol) was added to a mixture solution of 5,6-dimethyl-4-(1-methyl-1,2,3,4-tetrahydroisoquinolin-2-yl)-2-chloropyrimidine(1.4 g, 4.8 mmol) prepared in the above Step 2 and dimethylformamide (10 ml), 1.35 g of the titled compound was obtained in accordance with the same procedure as in Step 2 of Example 1.
Yield: 68%
M.P.: 201°–205° C.
$^1$H-NMR(DMSO-d$_6$): δ 1.58(d, 3H), 2.17(s, 3H), 2.36(s, 3H), 2.89(bd, 1H), 3.08(m, 1H), 3.59(m, 1H), 4.19(bd, 1H), 5.38(q, 1H), 7.34(m, 6H), 7.60(m, 2H), 10.40(s, 1H).

EXAMPLE 13

Synthesis of (R)-5,6-Dimethyl-2-(2-methyl-4-fluorophenylamino)-4-(1-methyl-1,2,3,4-tetrahydroisoquinolin-2-yl)pyrimidine hydrochloride Step 1: (R)-5,6-Dimethyl-4-(1-methyl-1,2,3,4-tetrahydroisoquinolin-2-yl)-2-chloropyrimidine In accordance with the same procedure as in Step 1 of Example 1, except that (R)-1-methyl-1,2,3,4-tetrahydroisoquinoline(3.9 g, 26.4 mmol) and 5,6-dimethyl-2,4-dichloropyridine(4.3 g, 24 mmol) were used as starting materials, 4.35 g of the titled compound was prepared. (Yield: 63%)

Step 2: (R)-5,6-Dimethyl-2-(2-methyl-4-fluorophenylamino)-4-(1-methyl-1,2,3,4-tetrahydroisoquinolin-2-yl)pyrimidine hydrochloride After 2-methyl-4-fluoroaniline(1.1 ml, 9.9 mmol) was added to a mixture solution of (R)-5,6-dimethyl-4-(1-methyl-1,2,3,4-tetrahydroisoquinolin-2-yl)-2-chloropyrimidine(1.4 g, 4.8 mmol) obtained in the above Step 1 and dimethylformamide(10 ml), 1.10 g of the titled compound was obtained in accordance with the same procedure as in Step 2 of Example 1.
Yield: 55.5%
M.P.: 203°–205° C.
$^1$H-NMR(DMSO-d$_6$): δ 1.58(d, 3H), 2.17(s, 3H), 2.36(s, 3H), 2.89(bd, 1H), 3.08(m, 1H), 3.59(m, 1H), 4.19(bd, 1H), 5.38(q, 1H), 7.34(m, 6H), 7.60(m, 2H), 10.40(s, 1H).

EXAMPLE 14

Synthesis of (S)-5,6-dimethyl-2-(2-methyl-4-fluorophenylamino)-4-(1-methyl-1,2,3,4-tetrahydroisoquinolin-2-yl)pyrimidine hydrochloride Step 1: (S)-5,6-Dimethyl-4-(1-methyl-1,2,3,4-tetrahydroisoquinolin-2-yl)-2-chloropyrimidine In accordance with the same procedure as in Step 1 of Example 1, except that (S)-1-methyl-1,2,3,4-tetrahydroisoquinoline(3.9 g, 26.4 mmol) and 5,6-dimethyl-2,4-dichloropyridine(4.3 g, 24 mmol) were used as starting materials, 4.2 g of the titled compound was prepared. (Yield: 60.8%)

Step 2: (S)-5,6-Dimethyl-2-(2-methyl-4-fluorophenylamino)-4-(1-methyl-1,2,3,4-tetrahydroisoquinolin-2-yl)pyrimidine hydrochloride After 2-methyl-4-fluoroaniline(1.1 ml, 9.9 mmol) was added to a mixture solution of (S)-5,6-dimethyl-4-(1-methyl-1,2,3,4-tetrahydroisoquinolin-2-yl)-2-chloropyrimidine(1.4 g, 4.8 mmol) obtained in the above Step 1 and dimethylformamide (10 ml), 0.90 g of the title compound was obtained in accordance with the same procedure as in Step 2 of Example 1.
Yield: 45.5%
M.P.: 202°–204° C.
$^1$H-NMR(DMSO-d$_6$): δ 1.58(d, 3H), 2.17(s, 3H), 2.36(s, 3H), 2.89(bd, 1H), 3.08(m, 1H), 3.59(m, 1H), 4.19(bd, 1H), 5.38(q, 1H), 7.34(m, 6H), 7.60(m, 2H), 10.40(s, 1H).

EXAMPLE 15

Synthesis of 5,6-dimethyl-2-(4-fluorophenylamino)-4-(1-methyl-1,2,3,4-tetrahydroisoquinolin-2-yl) pyrimidine hydrochloride After 4-fluoroaniline(1.0 ml, 10 mmol) was added to a mixture solution of 5,6-dimethyl-4-(1-methyl-1,2,3,4-tetrahydroisoquinolin-2-yl)-2-chloropyrimidine(1.4 g, 4.8 mmol) and dimethylformamide(10 ml), 1.32 g of the title compound was obtained in accordance with the same procedure as in Step 2 of Example 1.
Yield: 69%
M.P.: 205°–208° C.
$^1$H-NMR(DMSO-d$_6$): δ 1.58(d, 3H), 2.17(s, 3H), 2.36(s, 3H), 2.89(bd, 1H), 3.08(m, 1H), 3.59(m, 1H), 4.19(bd, 1H), 5.38(q, 1H), 7.34(m, 6H), 7.60(m, 2H), 10.40(s, 1H).

EXAMPLE 16

Synthesis of (R)-5,6-dimethyl-2-(4-fluorophenylamino)-4-(1-methyl-1,2,3,4-tetrahydroisoquinolin-2-yl)pyrimidine hydrochloride After 4-fluoroaniline(1 ml, 10 mmol) was added to a mixture solution of (R)-5,6-dimethyl-4-(1-methyl-1,2,3,4-tetrahydroisoquinolin-2-yl)-2-chloropyrimidine(1.4 g, 4.8 mmol) and dimethylformamide(10 ml), 1.20 g of the titled compound was obtained in accordance with the same procedure as in Step 2 of Example 1.
Yield: 62.7%
M.P.: 205°–207° C.
$^1$H-NMR(DMSO-d$_6$): δ 1.58(d, 3H), 2.17(s, 3H), 2.36(s, 3H), 2.89(bd, 1H), 3.08(m, 1H), 3.59(m, 1H), 4.19(bd, 1H), 5.38(q, 1H), 7.34(m, 6H), 7.60(m, 2H), 10.40(s, 1H).

EXAMPLE 17

Synthesis of (S)-5,6-dimethyl-2-(4-fluorophenylamino)-4-(1-methyl-1,2,3,4-tetrahydroisoquinolin-2-yl)pyrimidine hydrochloride After 4-fluoroaniline(1 ml, 10 mmol) was added to a mixture solution of (S)-5,6-dimethyl-4-(1-methyl-1,2,3,4-tetrahydroisoquinolin-2-yl)-2-chloropyrimidine(1.4 g, 4.8 mmol) and dimethylformamide(10 ml), 1.50 g of the titled compound was obtained in accordance with the same procedure as in Step 2 of Example 1.
Yield: 78.3%
M.P.: 204°–206° C.
$^1$H-NMR(DMSO-d$_6$): δ 1.58(d, 3H), 2.17(s, 3H), 2.36(s, 3H), 2.89(bd, 1H), 3.08(m, 1H), 3.59(m, 1H), 4.19(bd, 1H), 5.38(q, 1H), 7.34(m, 6H), 7.60(m, 2H), 10.40(s, 1H).

EXAMPLE 18

Synthesis of 5,6-dimethyl-2-(N-methylphenylamino)-4-(1-methyl-1,2,3,4-tetrahydroisoquinolin-2-yl)pyrimidine hydrochloride After N-methylaniline(1.5 ml, 14 mmol) was added to a mixture solution of 5,6-dimethyl-4-(1-methyl-1,2,3,4-tetrahydroisoquinolin-2-yl)-2-chloropyrimidine(1.9 g, 6.6 mmol) and dimethylformamide(10 ml), 0.25 g of the titled compound was obtained in accordance with the same procedure as in Step 2 of Example 1.
Yield: 9%
M.P.: 220°–222° C.
$^1$H-NMR(CDCl$_3$): δ 1.34(d, 3H), 2.19(s, 3H), 2.77(s, 3H), 2.93(bd, 2H), 3.48(m, 1H), 3.98(s, 3H), 4.04(bd, 1H), 5.02 (m, 1H), 6.88(m, 1H), 7.16–7.42(m, 5H), 7.58(m, 3H), 13.42(bd, 1H).

EXAMPLE 19

Synthesis of (R)-5,6-Dimethyl-2-(N-methylphenylamino)-4-(1-methyl-1,2,3,4-tetrahydroisoquinolin-2-yl)pyrimidine hydrochloride After N-methylaniline(1.04 ml, 9.6 mmol) was added to a mixture solution of (R)-5,6-dimethyl-4-(1-methyl-1,2,3,4-tetrahydroisoquinolin-2-yl)-2-chloropyrimidine(1.4 g, 4.8 mmol) and dimethyl formamide(10 ml), 0.55 g of the title compound was obtained in accordance with the same procedure as in Step 2 of Example 1.
Yield: 29%
M.P.: 221°–223° C.
$^1$H-NMR(CDCl$_3$): δ 1.34(d, 3H), 2.19(s, 3H), 2.77(s, 3H), 2.93(bd, 2H), 3.48(m, 1H), 3.98(s, 3H), 4.04(bd, 1H), 5.02 (m, 1H), 6.88(m, 1H), 7.16–7.42(m, 5H), 7.58(m, 3H), 13.42(bd, 1H).

EXAMPLE 20

Synthesis of (S)-5,6-dimethyl-2-(N-methylphenylamino)-4-(1-methyl-1,2,3,4-tetrahydroisoquinolin-2-yl)pyrimidine hydrochloride After N-methylaniline(1.04 ml, 9.6 mmol) was added to a mixture solution of (S)-5,6-dimethyl-4-(1-methyl-1,2,3,4-tetrahydroisoquinolin-2-yl)-2-chloropyrimidine(1.4 g, 4.8 mmol) and dimethylformamide(10 ml), 0.70 g of the titled compound was obtained in accordance with the same procedure as in Step 2 of Example 1.
Yield: 37%
M.P.: 220°–223° C.
$^1$H-NMR(CDCl$_3$): δ 1.34(d, 3H), 2.19(s, 3H), 2.77(s, 3H), 2.93(bd, 2H), 3.48(m, 1H), 3.98(s, 3H), 4.04(bd, 1H), 5.02 (m, 1H), 6.88(m, 1H), 7.16–7.42(m, 5H), 7.58(m, 3H), 13.42(bd, 1H).

EXAMPLE 21

Synthesis of 5,6-dimethyl-2-(phenylamino)-4-(1-methyl-1,2,3,4-tetrahydroisoquinolin-2-yl) pyrimidine hydrochloride After aniline(0.53 ml, 5.5 mmol) was added to a mixture solution of 5,6-dimethyl-4-(1-methyl-1,2,3,4-tetrahydroisoquinolin-2-yl)-2-chloropyrimidine(0.72 g, 2.5 mmol) and dimethylformamide(5 ml), 0.21 g of the titled compound was obtained in accordance with the same procedure as in Step 2 of Example 1.
Yield: 22%
M.P.: 243°–245° C.
$^1$H-NMR(DMSO-d$_6$): δ 1.58(d, 3H), 2.15(s, 3H), 2.34(s, 3H), 2.90(bd, 1H), 3.12(m, 1H), 3.64(m, 1H), 4.25(m, 1H), 5.42(q, 1H), 7.21(m, 5H), 7.43(m, 2H), 7.56(m, 2H), 10.30 (s, 1H), 13.35(bd, 1H).

EXAMPLE 22

Synthesis of (R)-5,6-Dimethyl-2-(4-phenylamino)-4-(1-methyl-1,2,3,4-tetrahydroisoquinolin-2-yl) pyrimidine hydrochloride After aniline(0.53 ml, 5.5 mmol) was added to a mixture solution of (R)-5,6-dimethyl-4-(1-methyl-1,2,3,4- tetrahydroisoquinolin-2-yl)-2-chloropyrimidine(0.72 g, 2.5 mmol) and dimethylformamide(5 ml), 0.25 g of the titled compound was obtained in accordance with the same procedure as in Step 2 of Example 1.
Yield: 26%
M.P.: 243°–246° C.
$^1$H-NMR(DMSO-d$_6$): δ 1.58(d, 3H), 2.15(s, 3H), 2.35(s, 3H), 2.89(bd, 1H), 3.12(m, 1H), 3.64(m, 1H), 4.25(m, 1H), 5.42(q, 1H), 7.20(m, 5H), 7.43(m, 2H), 7.56(m, 2H), 10.30 (s, 1H), 13.35(bd, 1H).

EXAMPLE 23

Synthesis of (S)-5,6-Dimethyl-2-(4-fluorophenylamino)-4-(1-methyl-1,2,3,4-tetrahydroisoquinolin-2-yl)pyrimidine hydrochloride After aniline(0.53 ml, 5.5 mmol) was added to a mixture solution of (S)-5,6-dimethyl-4-(1-methyl-1,2,3,4-tetrahydroisoquinolin-2-yl)-2-chloropyrimidine(0.72 g, 2.5 mmol) and dimethylformamide(5 ml), 0.20 g of the titled compound was obtained in accordance with the same procedure as in Step 2 of Example 1.
Yield: 21%
M.P.: 243°–245° C.
$^1$H-NMR(DMSO-d$_6$): δ 1.58(d, 3H), 2.15(s, 3H), 2.34(s, 3H), 2.89(bd, 1H), 3.12(m, 1H), 3.64(m, 1H), 4.25(m, 1H), 5.42(q, 1H), 7.20(m, 5H), 7.43(m, 2H), 7.56(m, 2H), 10.30 (s, 1H), 13.35(bd, 1H).

EXAMPLE 24

Synthesis of 5,6-Dimethyl-2-(2-methylphenylamino)-4-(1-methyl-1,2,3,4-tetrahydroisoquinolin-2-yl)pyrimidine hydrochloride After 2-methylaniline(1.0 ml, 9.6 mmol) was added to a mixture solution of 5,6-Dimethyl-4-(1-methyl-1,2,3,4-tetrahydroisoquinolin-2-yl)-2-chloropyrimidine(1.34 g, 4.6 mmol) and dimethylformamide(5 ml), 0.65 g of the titled compound was obtained in accordance with the same procedure as in Step 2 of Example 1.
Yield: 36%
M.P.: 94°–96° C.
$^1$H-NMR(DMSO-d$_6$): δ 1.52(d, 3H), 2.17(s, 3H), 2.30(s, 3H), 2.37(s, 3H), 2.82(d, 1H), 3.01(m, 1H), 3.54(t, 1H), 4.15(bd, 1H), 5.31(t, 1H), 7.15(m, 5H), 7.30(m, 2H), 7.73(d, 1H), 9.55(s, 1H), 13.73(bd, 1H).

EXAMPLE 25

Synthesis of 5,6-dimethyl-2-(4-methylphenylamino) -4-(1-methyl-1,2,3,4-tetrahydroisoquinolin-2-yl) pyrimidine hydrochloride After p-toluidine(0.45 g, 4.20 mmol) was added to a mixture solution of 5,6-dimethyl-4-(1-methyl-1,2,3,4-tetrahydroisoquinolin-2-yl)-2-chloropyrimidine(0.80 g, 2.78 mmol) and dimethylformamide(5 ml), 0.30 g of the titled compound was obtained in accordance with the same procedure as in Step 2 of Example 1.
Yield: 27%
M.P.: 243°–245° C.
$^1$H-NMR(CDCl$_3$): δ 1.64(d, 3H), 2.18(s, 3H), 2.36(s, 3H), 2.44(s, 3H), 2.87(bd, 1H), 3.28(tt, 1H), 3.60(tt, 1H), 4.30(bd, 1H), 5.42(q, 1H), 7.08–7.23(m, 6H), 7.52(d, 2H), 10.20(s, 1H), 14.10(bs, 1H).

EXAMPLE 26

Synthesis of 5-methyl-6-ethyl-2-(2-methyl-4-fluorophenylamino)-4-(1-methyl-1,2,3,4-tetrahydroisoquinolin-2-yl)pyrimidine hydrochloride
Step 1: 5-Methyl-6-ethyl-4-(1,2,3,4-tetrahydroisoquinolin-2-yl)-2-chloropyrimidine In accordance with the same procedure as in Step 1 of Example 1, except that 1-methyl-1,2,3,4-tetrahydroisoquinoline (2.3 g, 15.6 mmol) and 2,4-dichloro-5-methyl-6-ethylpyrimidine (2.7 g, 14.1 mmol) prepared in Preparation 4 were used as starting materials, 2.3 g of the titled compound was prepared. (Yield: 54%)
Step 2: 5-Methyl-6-ethyl-2-(2-methyl-4-fluorophenylamino)-4-(1-methyl-1,2,3,4-tetrahydroisoquinolin-2-yl)pyrimidine hydrochloride After 4-fluoro-2-methylaniline(0.55 ml, 4.95 mmol) was added to a mixture solution of 5-methyl-6-ethyl-4-(1,2,3,4-tetrahydroisoquinolin-2-yl)-2-chloropyrimidine(0.80 g, 2.65 mmol) and dimethylformamide (5 ml), 0.25 g of the titled compound was obtained in accordance with the same procedure as in Step 2 of Example 1.
Yield: 22.1%
M.P.: 171°–173° C.
$^1$H-NMR(DMSO-d$_6$): δ 1.20(t, 3H), 1.46(d, 3H), 2.16(s, 3H), 2.22(s, 3H), 2.68(q, 2H), 2.95(m, 1H), 3.48(t, 1H), 4.12(d, 2H), 5.20(q, 1H), 6.90–7.30(m, 6H), 7.58(m, 1H).

EXAMPLE 27

Synthesis of 5-methyl-6-ethyl-2-(4-fluorophenylamino)-4-(1-methyl-1,2,3,4-tetrahydroisoquinolin-2-yl)pyrimidine hydrochloride After 4-fluoroaniline(0.50 ml, 5.28 mmol) was added to a mixture solution of 5-methyl-6-ethyl-4-(1-methyl-1,2,3,4-tetrahydroisoquinolin-2-yl)-2-chloropyrimidine (0.80 g, 2.65 mmol) and dimethylformamide(5 ml), 0.55 g of the titled compound was obtained in accordance with the same procedure as in Step 2 of Example 1.
Yield: 50.3%
M.P.: 198°–200° C.
$^1$H-NMR(DMSO-d$_6$): δ 1.20(t, 3H), 1.56(d, 3H), 2.18(s, 3H), 2.56(q,2H), 2.81(bd, 1H), 3.05(m, 1H), 3.58(t, 1H), 4.41(d, 1H), 5.38(q, 1H), 7.00–7.40(m, 6H), 7.58(m, 2H).

EXAMPLE 28

Synthesis of 5-methyl-6-ethyl-2-(N-methylphenylamino)-4-(1-methyl-1,2,3,4-tetrahydroisoquinolin-2-yl)pyrimidine hydrochloride After N-methylaniline(0.44 ml, 4.06 mmol) was added to a mixed solution of 5-methyl-6-ethyl-4-(1-methyl-1,2,3,4-tetrahydroisoquinolin-2-yl)-2-chloropyrimidine(0.80 g, 2.65 mmol) and dimethylformamide(5 ml), 0.60 g of the titled compound was obtained in accordance with the same procedure as in Step 2 of Example 1.
Yield: 55.4%
M.P.: 214°–216° C.
$^1$H-NMR(DMSO-d$_6$): δ 1.90(t, 3H), 1.46(d, 3H), 2.18(s, 3H), 2.67(q, 2H), 2.79(bs, 2H), 2.90–3.18(m, 1H), 3.40–3.60(S+m, 4H), 4.18(dd, 1H), 5.25(q, 1H), 7.05–7.20 (s, 4H), 7.32–7.58(m, 5H).

EXAMPLE 29

Synthesis of 2-(2-methyl-4-fluorophenylamino)-4-(1-methyl-1,2,3,4-tetrahydroisoquinolin-2-yl) cyclopenta[d]pyrimidine hydrochloride
Step 1: 2-Amino-4-hydroxycyclopenta[d]pyrimidine A solution of 2-ethoxycarbonyl cyclopentanone (114 ml, 0.77mol) and N,N-dimethylformamide (40 ml) was added dropwise to a mixture solution of sodium methoxide(83.2 g, 0.44 mol) and N,N-dimethylformamide(80 ml), while maintaining the temperature of the reaction system below 0° C.

A solution of guanidine HCl salt(81 g, 0.85 mol) and methanol(127 ml) was added to the above reaction mixture and then was heated to reflux for 14 hours. The reaction mixture was neutralized by conc. HCl and the resulting solid was filtered and dried under reduced pressure to give 20.69 g of titled compound.
(Yield: 18%)

Step 2: 2,4-Dihydroxycyclopenta[d]pyrimidine

To a mixture solution of 20% HCl(62 ml) and 2-amino-4-hydroxycyclopenta[d]pyrimidine (20.6 g, 0.136 mol) prepared in the above Step 1 was added aqueous solution of sodium nitrite (19.4 g) for 4 hours while keeping the temperature of the reaction system at 70° C. The reaction mixture was cooled to 0° C. and the resulting solid was filtered, dried under reduced pressure to give 15.43 g of titled compound.
(Yield: 74.6%)

Step 3: 2,4-dichlorocyclopenta[d]pyrimidine

A mixture solution of phosphorous oxychloride(49 ml), N,N-dimethylaniline(8.0 ml) and 2,4-dihydroxycyclopenta[d]pyrimidine(15.4 g, 0.1 mol) prepared in the above Step 2 was heated to reflux for 3 hours and cooled to a room temperature. After the reaction mixture was diluted with dichloromethane, the diluted solution was added to ice water, while maintaining the temperature of the reaction system below 10° C. The reaction mixture was extracted with dichloromethane, dried over anhydrous sodium sulfate and concentrated in vacuo to give 2.8 g of titled compound as an oily form. (Yield: 15%)

Step 4: 4-(1-Methyl-1,2,3,4-tetrahydroisoquinolin-2-yl)-2-chlorocyclopenta[d]pyrimidine In accordance with the same procedure as in Step 1 of Example 1, except that 1-methyl-1,2,3,4-tetrahydroisoquinoline(1.7 g, 11.55 mmol) and 2,4-dichlorocyclopenta[d]pyrimidine(2.0 g, 10.5 mmol) prepared in the above Step 3 were used as starting materials, 1.95 g of the title compound was prepared. (Yield: 62%)

Step 5: 2-(2-Methyl-4-fluorophenylamino)-4-(1-methyl-1,2,3,4-tetrahydroisoquinolin-2-yl)cyclopenta[d]pyrimidine hydrochloride After 4-fluoro-2-methylaniline(0.40 ml, 3.60 mmol) was added to a mixture solution of 4-(1-methyl-1,2,3,4-tetrahydroisoquinolin-2-yl)-2-chlorocyclopenta[d]pyrimidine (0.50 g, 1.70 mmol) and dimethylformamide(5 ml), 0.15 g of the titled compound was obtained in accordance with the same procedure as in Step 2 of Example 1.
Yield: 20.8%
M.P.: 110°–112° C.
$^1$H-NMR(DMSO-d$_6$): δ 1.50(t, 3H), 2.12(m, 2H), 2.25(s, 3H), 2.93(bd, 3H), 3.10(m, 2H), 3.42(bd, 2H), 3.70(bd, 1H), 4.40(bd, 1H), 5.78(bd, 1H), 7.22(m, 6H), 7.50(m, 5H), 7.60(m, 1H), 9.80(s, 1H), 13.32(bd, 1H).

EXAMPLE 30

Synthesis of 2-(4-fluorophenylamino)-4-(1-methyl-1,2,3,4-tetrahydroisoquinolin-2-yl)cyclopenta[d] pyrimidine hydrochloride After 4-fluoroaniline(0.40 ml, 4.2 mmol) was added to a mixture solution of 4-(1-methyl-1,2,3,4-tetrahydroisoquinoline-2-yl)-2-chlorocyclopenta[d]pyrimidine(0.60 g, 2.0 mmol) and dimethylformamide(5 ml), 0.11 g of the titled compound was obtained in accordance with the same procedure as in Step 2 of Example 1.
Yield: 13.4%
M.P.: 220°–222° C.
$^1$H-NMR(DMSO-d$_6$): δ 1.58(d, 3H), 2.10(bd, 2H), 3.01(bd, 4H), 3.18(m, 2H), 3.60(bd, 1H), 4.45(bd, 1H), 5.64(bd, 1H), 7.30(m, 6H), 7.62(m, 2H), 10.42(s, 1H), 13.15(bd, 1H).

EXAMPLE 31

Synthesis of 2-(N-methylphenylamino)-4-(1-methyl-1,2,3,4-tetrahydroisoquinolin-2-yl)cyclopenta[d] pyrimidine hydrochloride After N-methylaniline(0.20 ml, 1.90 mmol) was added to a mixture solution of 4-(1-methyl-1,2,3,4-tetrahydroisoquinolin-2-yl)-2-chlorocyclopenta[d] pyrimidine (0.51 g, 1.70 mmol) and dimethylformamide(5 ml), 0.20 g of the titled compound was obtained in accordance with the same procedure as in Step 2 of Example 1.
Yield: 29%
M.P.: 105°–107° C.
$^1$H-NMR(DMSO-d$_6$): δ 1.42(bd, 3H), 2.10(m, 2H), 2.87(m, 5H), 3.10(m, 2H), 3.58(s, 3H), 4.38(bd, 1H), 5.53(q, 1H), 7.21(m, 4H), 7.48(m, 5H), 12.62(bd, 1H).

EXAMPLE 32

Synthesis of 2-(2-methyl-4-fluorophenylamino)-4-(1-methyl-1,2,3,4-tetrahydroisoquinolin-2-yl)-5,6,7,8-tetrahydroquinazoline hydrochloride Step 1: 2,4-Dihydroxy-5,6,7,8-tetrahydroquinazoline A mixture solution of 2,4-dihydroxyquinazoline(39.2 g, 0.24 mol), platinium oxide(4 g) and trifluoroacetic acid(300 ml) was hydrogenated by Parr reactor for 2 hours. Platinium was filtered and the filtrate was concentrated, diluted with water, and basified with 1N-NaOH solution. The resulting solid was filtered and dried to give 13.76 g of the titled compound. (Yield: 34.5%)

Step 2: 2,4-Dichloro-5,6,7,8-tetrahydroquinazoline 2,4-Dihydroxy-5,6,7,8-tetrahydroquinazoline(3.4 g, 20 mmol) prepared in the above Step 1 was suspended in a mixture solution of phosphorous oxychloride(10 mL) and N,N-dimethylaniline(0.8 ml). The reaction mixture was heated to reflux for 3 hours and cooled to room temperature. The reaction mixture was added to ice water while maintaining the temperature of the reaction system below 10° C. and the resulting solid was filtered, dried under reduced pressure to give 3.26 g of the titled compound.
(Yield: 80%)

Step 3: 4-(1-Methyl-1,2,3,4-tetrahydroisoquinolin-2-yl)-2-chloro-5,6,7,8-tetrahydroquinazoline A mixture solution of 1-methyl-1,2,3,4-tetrahydroisoquinoline(2.6 g, 17.4 mmol), triethylamine(2.8 mL), N,N-dimethylformamide (20 ml) and 2,4-dichloro-5,6,7,8-tetrahydroquinazoline(3.2 g, 15.8 mmol) prepared in the above Step 2 were stirred at 80° C. for 3 hours and cooled. The reaction mixture was diluted with ethyl acetate and washed with water. The organic layer was separated, dried over anhydrous sodium sulfate, and concentrated. The residue was purified with silica gel column chromatography to give 3.1 g of the titled compound. (Yield: 62.5%)

Step 4: 2-(2-Methyl-4-fluorophenylamino)-4-(1-methyl-1,2,3,4-tetrahydroisoquinolin-2-yl)-5,6,7,8-tetrahydroquinazoline hydrochloride After 4-fluoro-2-methylaniline(0.60 ml, 5.4 mmol) was added to a mixture solution of 4-(1-methyl-1,2,3,4-tetrahydroisoquinolin-2-yl)-2-chloro-5,6,7,8-tetrahydroquinazoline(0.75 g, 2.40 mmol) and dimethylformamide(5 ml), 0.58 g of the titled compound was obtained in accordance with the same procedure as in Step 2 of Example 1.
Yield: 55%
M.P.: 190°–193° C.
$^1$H-NMR(DMSO-d$_6$): δ 1.53(d, 3H), 1.60–1.96(m, 3H), 2.34(s, 3H), 2.55(bd, 2H), 2.75(bd, 4H), 2.98(m, 1H), 3.54

(m, 1H), 4.25(bd, 1H), 5.36(q, 1H), 7.12–7.31(m, 6H), 7.60(m, 1H), 9.69(s, 1H).

EXAMPLE 33

Synthesis of 2-(N-methylphenylamino)-4-(1-methyl-1,2,3,4-tetrahydroisoquinoline-2-yl)-5,6,7,8-tetrahydroquinazoline hydrochloride After N-methylaniline(0.50 ml, 4.8 mmol) was added to a mixture solution of 4-(1-methyl-1,2,3,4-tetrahydroisoquinolin-2-yl)-2-chloro-5,6,7,8-tetrahydroquinazoline(0.75 g, 2.40 mmol) and dimethylformamide(5 ml), 0.26 g of the titled compound was obtained in accordance with the same procedure as in Step 2 of Example 1.
Yield: 26%
M.P.: 207°–210° C.
$^1$H-NMR(DMSO-d$_6$): δ 1.42(d, 3H), 1.53–1.96(m, 3H), 2.57(bd, 1H), 2.80(m, 5H), 2.95(m, 1H), 3.45(bd, 1H), 3.60(s, 3H), 4.18(bd, 1H), 5.25(q, 1H), 7.16(m, 3H), 7.50(m, 6H), 12.10(s, 1H).

EXAMPLE 34

Synthesis of 6-methyl-2-(2-methyl-4-fluorophenylamino)-4-(1,2,3,4-tetrahydroisoquinolin-2-yl)pyrimidine hydrochloride Step 1: 6-methyl-4-(1,2,3,4-tetrahydroisoquinolin-2-yl)-2-chloropyrimidine In accordance with the same procedure as in Step 1 of Example 1, except that 6-methyl-2,4-dichloropyrimidine (3.26 g, 20 mmol), 1,2,3,4-tetrahydroisoquinoline(2.6 ml, 20.5 mmol), triethylamine(3.4 ml, 24.4 mmol) and N,N-dimethyl formamide (10 ml) were used as starting materials, 3.1 g of the titled compound was prepared. (Yield: 59.7%)

Step 2: 6-Methyl-2-(2-methyl-4-fluorophenylamino)-4-(1,2,3,4-tetrahydroisoquinolin-2-yl)pyrimidine hydrochloride After 2-methyl-4-fluoroaniline(0.8 ml, 7.2 mmol) was added to a mixture solution of 6-methyl-4-(1,2,3,4-tetrahydroisoquinoline-2-yl)-2-chloropyrimidine(1.0 g, 3.8 mmol) and dimethylformamide(10 ml), 0.85 g of the titled compound was obtained in accordance with the same procedure as in Step 2 of Example 1.
Yield: 58%
M.P.: 183°–185° C.
$^1$H-NMR(CDCl$_3$): δ 2.41(s, 3H), 2.48(d, 3H), 2.88(t, 1H), 3.02(t, 1H), 3.75(t, 1H), 3.91(t, 1H),4.67(s, 1H), 4.78(s, 1H), 6.00(d, 1H), 6.90–7.30(m, 5H), 7.58(m, 1H), 9.75(s, 1H), 14.20(bs, 1H).

EXAMPLE 35

Synthesis of 6-methyl-2-(4-fluorophenylamino)-4-(1,2,3,4-tetrahydroisoquinoline-2-yl)pyrimidine hydrochloride After 4-fluoroaniline(0.7 ml, 7.4 mmol) was added to a mixture solution of 6-methyl-4-(1,2,3,4-tetrahydroisoquinoline-2-yl)-2-chloropyrimidine(1.0 g, 3.8 mmol) and dimethylformamide(10 ml), 0.6 g of the titled compound was obtained in accordance with the same procedure as in Step 2 of Example 1.
Yield: 42.6%
M.P.: 238°–240° C.
$^1$H-NMR(CDCl$_3$): δ 2.45(d, 3H), 2.90–3.10(m, 2H), 3.78(t, 1H), 4.05(t, 1H), 4.70(s, 1H), 4.92(t, 1H), 6.05(d, 1H), 6.90–7.30(m, 6H), 7.60(m, 2H), 10.40(s, 1H), 13.80(bs, 1H).

EXAMPLE 36

Synthesis of 6-methyl-2-(N-methylphenylamino)-4-(1,2,3,4-tetrahydroisoquinolin-2-yl)pyrimidine hydrochloride After N-methylaniline(0.61 ml, 5.48 mmol) was added to a mixture solution of 6-methyl-4-(1,2,3,4-tetrahydroisoquinolin-2-yl)-2-chloropyrimidine(0.95 g, 3.65 mmol) and dimethylformamide(10 ml), 0.7 g of the titled compound was obtained in accordance with the same procedure as in Step 2 of Example 1.
Yield: 52.3%
M.P.: 85°–95° C.
$^1$H-NMR(CDCl$_3$): δ 2.75(s, 3H), 2.99(s, 3H), 3.70(m, 2H), 3.87(s, 3H), 4.51(s, 1H), 4.65(s, 1H), 5.30(bs, 1H), 6.08(d, 1H), 6.88(d, 1H), 7.05–7.60(m, 8H), 13.05(s, 1H).

EXAMPLE 37

Synthesis of 6-ethyl-2-(2-methyl-4-fluorophenylamino)-4-(1,2,3,4-tetrahydroisoquinolin-2-yl)pyrimidine hydrochloride Step 1: 6-Ethyl-4-(1,2,3,4-tetrahydroisoquinolin-2-yl)-2-chloropyrimidine In accordance with the same procedure as in Step 1 of Example 1, except that 1,2,3,4-tetrahydroisoquinoline(3.5 ml, 28 mmol), triethylamine(3.9 ml, 28 mmol),N,N-dimethylformamide (20 ml) and 6-ethyl-2,4-dichloropyrimidine(4.9 g, 27.7 mmol) prepared in Preparation 2 were used as starting materials, 5.0 g of the titled compound was prepared. (Yield: 66%)

Step 2: 6-Ethyl-2-(2-methyl-4-fluorophenylamino)-4-(1,2,3,4-tetrahydroisoquinolin-2-yl)pyrimidine hydrochloride After 2-methyl-4-fluoroaniline(0.57 ml, 5.13 mmol) was added to a mixture solution of 6-ethyl-4-(1,2,3,4-tetrahydroisoquinoline-2-yl)-2-chloropyrimidine(0.7 g, 2.56 mmol) and dimethylformamide(5 ml), 0.55 g of the titled compound was obtained in accordance with the same procedure as in Step 2 of Example 1.
Yield: 54%
M.P.: 223°–225° C.
$^1$H-NMR(CDCl$_3$): δ 1.36(qq, 3H), 2.35(s, 3H), 2.69(tt, 2H), 2.90(tt, 2H), 3.77(tt, 2H), 4.66(ss, 2H), 5.93(d, 2H), 6.72–7.30(m, 6H), 7.50(dd, 1H), 9.80(s, 1H), 14.00(s, 1H).

EXAMPLE 38

Synthesis of 6-ethyl-2-(4-fluorophenylamino)-4-(1,2,3,4-tetrahydroisoquinolin-2-yl)pyrimidine hydrochloride After 4-fluoroaniline(0.50 ml, 5.28 mmol) was added to a mixture solution of 6-ethyl-4-(1,2,3,4-tetrahydroisoquinoline-2-yl)-2-chloropyrimidine(0.7 g, 2.56 mmol) and dimethylformamide(5 ml), 0.41 g of the titled compound was obtained in accordance with the same procedure as in Step 2 of Example 1.
Yield: 42%
M.P.: 203°–206° C.
$^1$H-NMR(CDCl$_3$): δ 1.42(tt, 3H), 2.74(qq, 2H), 3.02(tt, 2H), 3.93(tt, 2H), 4.82(ss, 2H), 6.03(ss, 2H), 7.00–7.32(m, 6H), 7.54–7.64(m, 2H), 10.60(s, 1H), 13.80(s, 1H).

EXAMPLE 39

Synthesis of 6-ethyl-2-(N-methylphenylamino)-4-(1,2,3,4-tetrahydroisoquinolin-2-yl)pyrimidine hydrochloride After N-methylaniline(0.54 ml, 5.15 mmol) was added to a mixture solution of 6-ethyl-4-(1,2,3,4- tetrahydroisoquinoline-2-yl)-2-chloropyrimidine(0.7 g, 2.56 mmol) and dimethylformamide(5 ml), 0.56 g of the titled compound was obtained in accordance with the same procedure as in Step 2 of Example 1.
Yield: 57%
M.P.: 98°–100° C.
$^1$H-NMR(CDCl$_3$): δ 1.24–1.40(m, 3H), 2.83(tt, 2H), 3.16–3.24(m, 2H), 3.65(tt, 2H), 3.89(s, 3H), 4.53(ss, 2H), 6.00(ss, 1H), 6.85(d, 1H), 7.05–7.55(m, 8H), 13.40(s, 1H).

EXAMPLE 40

Synthesis of 6-ethyl-2-(2-methylphenylamino)-4-(1,2,3,4-tetrahydroisoquinolin-2-yl)pyrimidine hydrochloride After 2-methylaniline(0.55 ml, 5.15 mmol) was added to a mixture solution of 6-ethyl-4-(1,2,3,4-tetrahydroisoquinoline-2-yl)-2-chloropyrimidine(0.7 g, 2.56 mmol) and dimethylformamide(5 ml), 0.23 g of the titled compound was obtained in accordance with the same procedure as in Step 2 of Example 1.
Yield: 24%
M.P.: 153°–155° C.
$^1$H-NMR(CDCl$_3$): δ 1.37–1.47(m, 3H), 2.50(s, 3H), 2.74–2.76(m, 2H), 2.97(tt, 2H), 3.87(tt, 2H), 4.76(ss, 2H), 5.98(ss, 1H), 7.10–7.28(m, 7H), 7.70(t, 1H), 9.82(s, 1H), 14.17(s, 1H).

EXAMPLE 41

Synthesis of 5,6-dimethyl-2-(2-methyl-4-fluorophenylamino)-4-(1,2,3,4-tetrahydroisoquinolin-2-yl)pyrimidine hydrochloride Step 1: 5,6-dimethyl-4-(1,2,3,4-tetrahydroisoquinolin-2-yl)-2-chloropyrimidine In accordance with the same procedure as in Step 1 of Example 1, except that 1,2,3,4-tetrahydroisoquinoline(2.9 g, 23 mmol) and 5,6-dimethyl-2,4-dichloropyrimidine(3.8 g, 21 mmol) and 1,2,3,4-tetrahydroisoquinoline(2.9 g, 23 mmol) prepared in Step 1 of Example 12 were used as starting materials, 3.95 g of the titled compound was prepared.
(Yield: 68.7%)

Step 2: 5,6-Dimethyl-2-(2-methyl-4-fluorophenylamino)-4-(1,2,3,4-tetrahydroisoquinolin-2-yl)pyrimidine hydrochloride After 4-fluoro-2-methylaniline(0.8 ml, 7 mmol) was added to a mixture solution of 5,6-dimethyl-4-(1,2,3,4-tetrahydroisoquinoline-2-yl)-2-chloropyrimidine(1.0 g, 3.6 mmol) and dimethylformamide(10 ml), 0.58 g of the titled compound was obtained in accordance with the same procedure as in Step 2 of Example 1.
Yield: 44%
M.P.: 190°–193° C.
$^1$H-NMR(DMSO-d$_6$): δ 2.17(s, 3H), 2.30(s, 3H), 2.36(s, 3H), 2.90(t, 2H), 3.80(t, 1H), 4.75(s, 2H), 7.08–7.19(m, 6H), 7.70(m, 1H), 9.63(s, 1H), 13.62(s, 1H).

EXAMPLE 42

Synthesis of 5,6-dimethyl-2-(4-fluorophenylamino)-4-(1,2,3,4- tetrahydroisoquinolin-2-yl)pyrimidine hydrochloride After 4-fluoroaniline(0.7 ml, 7.4 mmol) was added to a mixture solution of 5,6-dimethyl-4-(1,2,3,4-tetrahydroisoquinolin-2-yl)-2-chloropyrimidine(1.0 g, 3.6 mmol) and dimethylformamide(5 ml), 0.67 g of the titled compound was obtained in accordance with the same procedure as in Step 2 of Example 1.
Yield: 48%
M.P.: 251°–253° C.
$^1$H-NMR(DMSO-d$_6$): δ 2.23(s, 3H), 2.41(s, 3H), 3.02(t, 2H), 3.94(t, 2H), 4.87(s, 2H), 7.35(m, 6H), 7.65(m, 2H), 10.39(s, 1H), 13.20(bd, 1H).

EXAMPLE 43

Synthesis of 5,6-dimethyl-2-(N-methylphenylamino)-4-(1,2,3,4-tetrahydroisoquinolin-2-yl)pyrimidine hydrochloride After N-methylaniline(0.84 ml, 7.8 mmol) was added to a mixture solution of 5,6-dimethyl-4-(1,2,3,4-tetrahydroisoquinolin-2-yl)-2-chloropyrimidine(1.0 g, 3.6 mmol) and dimethylformamide(5 ml), 0.55 g of the titled compound was obtained in accordance with the same procedure as in Step 2 of Example 1.
Yield: 39%
M.P.: 58°–60° C.
$^1$H-NMR(DMSO-d$_6$): δ 2.14(s, 3H), 2.45(s, 3H), 2.83(t, 2H), 3.64(s, 3H), 3.71(t, 2H), 4.66(s, 2H), 7.07–7.15(m, 4H), 7.38–7.54(m, 5H), 12.40(s, 1H).

EXAMPLE 44

Synthesis of 5-methyl-6-ethyl-2-(2-methyl-4-fluorophenylamino)-4-(1,2,3,4-tetrahydroisoquinolin-2-yl)pyrimidine hydrochloride Step 1: 5-Methyl-6-ethyl-4-(1,2,3,4-tetrahydroisoquinolin-2-yl)-2-chloropyrimidine In accordance with the same procedure as in Step 1 of Example 1, except that 1,2,3,4-tetrahydroisoquinoline(3.5 ml, 28 mmol) and 2,4-dichloro-5-methyl-6-ethylpyrimidine (4.9 g, 27.7 mmol) prepared in Preparation 4 were used as starting materials, 5.0 g of the titled compound was prepared.
(Yield: 66%)

Step 2: 5-Methyl-6-ethyl-2-(2-methyl-4-fluorophenylamino)-4-(1,2,3,4-tetrahydroisoquinolin-2-yl) pyrimidine hydrochloride After 4-fluoro-2-methylaniline(0.5 ml, 3.6 mmol) was added to a mixture solution of 5-methyl-6-ethyl-4-(1,2,3,4-tetrahydroisoquinolin-2-yl)-2-chloropyrimidine(0.7 g, 2.4 mmol) and dimethylformamide(5 ml), 0.53 g of the titled compound was obtained in accordance with the same procedure as in Step 2 of Example 1.
Yield: 53.5%
M.P.: 192°–194° C.
$^1$H-NMR(DMSO-d$_6$): δ 1.25(t, 3H), 2.19(s, 3H), 2.28(s, 3H), 2.68(q, 2H), 2.88(t, 2H), 3.79(t, 2H), 4.75(s, 2H), 7.15(m, 6H), 7.70(m, 1H), 9.80(s, 1H).

EXAMPLE 45

Synthesis of 5-methyl-6-ethyl-2-(4-fluorophenylamino)-4-(1,2,3,4-tetrahydroisoquinolin-2-yl)pyrimidine hydrochloride After 4-fluoroaniline(0.45 ml, 3.6 mmol) was added to a mixture solution of 5-methyl-6-ethyl-4-(1,2,3,4-tetrahydroisoquinolin-2-yl)-2-chloropyrimidine(0.7 g, 2.4 mmol) and dimethylformamide(5 ml), 0.50 g of the titled compound was obtained in accordance with the same procedure as in Step 2 of Example 1.
Yield: 52.2%
M.P.: 235°–238° C.

¹H-NMR(CDCl₃): δ 1.42(t, 3H), 2.25(s, 3H), 2.76(q, 2H), 3.04(t, 2H), 3.90(t, 2H), 4.80(s, 2H), 6.95–7.35(m, 6H), 7.55(m, 2H), 10.50(s, 1H), 13.80(bd, 1H).

EXAMPLE 46

Synthesis of 5-methyl-6-ethyl-2-(N-methylphenylamino)-4-(1,2,3,4-tetrahydroisoquinolin-2-yl)pyrimidine hydrochloride After N-methylaniline(0.40 ml, 3.6 mmol) was added to a mixture solution of 5-methyl-6-ethyl-4-(1,2,3,4-tetrahydroisoquinolin-2-yl)-2-chloropyrimidine(0.7 g, 2.4 mmol) and dimethylformamide(5 ml), 0.50 g of the titled compound was obtained in accordance with the same procedure as in Step 2 of Example 1.
Yield: 52.7%
M.P.: 75°–80° C.
¹H-NMR(CDCl₃): δ 1.32(t, 3H), 2.15(s, 3H), 2.80(t, 2H), 3.10(m, 2H), 3.60(m, 2H), 3.80(s, 3H), 4.48(s,2H), 6.95(m, 2H), 7.05–7.70(m, 7H).

EXAMPLE 47

Synthesis of 2-(2-methyl-4-fluorophenylamino)-4-(1,2,3,4-tetrahydroisoquinolin-2-yl)cyclopenta[d]pyrimidine hydrochloride Step 1: 4-(1,2,3,4-Tetrahydroisoquinolin-2-yl)-2-chlorocyclopenta[d]pyrimidine In accordance with the same procedure as in Step 1 of Example 1, except that 1,2,3,4-tetrahydroisoquinoline(0.5 ml, 4 mmol) and 2,4-dichlorocyclopenta[d]pyrimidine(0.79 g, 4 mmol) prepared in Step 3 of Example 29 were used as starting materials, 0.58 g of the titled compound was prepared.
(Yield: 51%)

Step 2: 2-(2-Methyl-4-fluorophenylamino)-2-(1,2,3,4-tetrahydroisoquinolin-2-yl)cyclopenta[d]pyrimidine hydrochloride After 4-fluoro-2-methylaniline(0.25 ml, 2.20 mmol) was added to a mixture solution of 4-(1,2,3,4-tetrahydroisoquinolin-2-yl)-4-chlorocyclopenta[d]pyrimidine(0.58 g, 2.0 mmol) and dimethylformamide(5 ml), 0.34 g of the titled compound was obtained in accordance with the same procedure as in Step 2 of Example 1.
Yield: 41.4%
M.P.: 170°–172° C.
¹H-NMR(DMSO-d₆): δ 2.06(m, 2H), 2.26(s, 3H), 2.90(m, 4H), 3.12(t, 2H), 3.97(t, 2H), 4.90(s, 2H), 7.11–7.21(m, 6H), 9.78(s, 1H), 13.25(bd, 1H).

EXAMPLE 48

Synthesis of 2-(2-methyl-4-fluorophenylamino)-4-(1,2,3,4-tetrahydroisoquinolin-2-yl)-5,6,7,8-tetrahydroquinazoline hydrochloride Step 1: 4-(1,2,3,4-tetrahydroisoquinolin-2-yl)-2-chloro-5,6,7,8-tetrahydroquinazoline hydrochloride In accordance with the same procedure as in Step 1 of Example 1, except that a mixture solution of 1,2,3,4-tetrahydroisoquinoline(2.8 ml, 22 mmol), triethylamine(3.4 ml, 24 mmol), N,N-dimethylformamide(10 ml) and 2,4-dichloro-5,6,7,8-tetrahydroquinazoline(4.0 g, 20 mmol) prepared in Step 2 of Example 32 were used as starting materials, 4.7 g of the titled compound was prepared. (Yield: 78.4%)

Step 2: 2-(2-Methyl-4-fluorophenylamino)-4-(1,2,3,4-tetrahydroisoquinolin-2-yl)-5,6,7,8-tetrahydroquinazoline hydrochloride After 4-fluoro-2-methylaniline(0.75 ml, 6.6 mmol) was added to a mixture solution of 4-(1,2,3,4-tetrahydroisoquinolin-2-yl)-2-chloro-5,6,7,8-tetrahydroquinazoline(0.90 g, 3.0 mmol) and dimethylformamide(5 ml), 0.36 g of the titled compound was obtained in accordance with the same procedure as in Step 2 of Example 1.
Yield: 28%
M.P.: 191°–193° C.
¹H-NMR(DMSO-d₆): δ 1.62–1.80(bd, 4H), 2.26(s, 3H), 2.65(bd, 4H), 2.88(t, 2H), 3.84(t, 2H), 4.78(s, 2H), 7.18(m, 6H), 7.67(m, 1H), 9.72(s, 1H), 13.40(bd, 1H).

EXAMPLE 49

Synthesis of 2-(4-fluorophenylamino)-4-(1,2,3,4-tetrahydroisoquinolin-2-yl)-5,6,7,8-tetrahydroquinazoline hydrochloride After 4-fluoroaniline(0.60 ml, 6.3 mmol) was added to a mixture solution of 4-(1,2,3,4-tetrahydroisoquinolin-2-yl)-2-chloro-5,6,7,8-tetrahydroquinazoline(0.90 g, 3.0 mmol) and dimethylformamide(5 ml), 0.62 g of the titled compound was obtained in accordance with the same procedure as in Step 2 of Example 1.
Yield: 50%
M.P.: 215°–218° C.
¹H-NMR(DMSO-d₆): δ 1.62–1.74(bd, 4H), 2.68(m, 4H), 2.95(t, 2H), 3.90(t, 2H), 4.86(s, 2H), 7.19–7.41(m, 6H), 7.57(m, 2H), 10.42(s, 1H), 11.40(bd, 1H).

EXAMPLE 50

Synthesis of 2-(N-methylphenylamino)-4-(1,2,3,4-tetrahydroisoquinolin-2-yl)-5,6,7,8-tetrahydroquinazoline hydrochloride After N-methylaniline(0.70 ml, 6.3 mmol) was added to a mixture solution of 4-(1,2,3,4-tetrahydroisoquinolin-2-yl)-2-chloro-5,6,7,8-tetrahydroquinazoline(0.90 g, 3.0 mmol) and dimethylformamide(5 ml), 0.48 g of the titled compound was obtained in accordance with the same procedure as in Step 2 of Example 1.
Yield: 39%
M.P.: 164°–167° C.
¹H-NMR(DMSO-d₆): δ 1.59–1.74(bd, 4H), 2.64(t, 2H), 2.78(m, 4H), 3.51(s, 3H), 3.78(t, 2H), 4.72(s, 2H), 7.19–7.17(m, 4H), 7.38–7.50(m, 5H), 12.18(bd, 1H).

EXAMPLE 51

Synthesis of 2-(2-methylphenylamino)-4-(1,2,3,4-tetrahydroisoquinolin-2-yl)-5,6,7,8-tetrahydroquinazoline hydrochloride After 2-methylaniline(0.30 ml, 2.7 mmol) was added to a mixture solution of 4-(1,2,3,4-tetrahydroisoquinolin-2-yl)-2-chloro-5,6,7,8-tetrahydroquinazoline(0.75 g, 2.5 mmol) and dimethylformamide(5 ml), 0.50 g of the titled compound was obtained in accordance with the same procedure as in Step 2 of Example 1.
Yield: 49%
M.P.: 173°–175° C.
¹H-NMR(DMSO-d₆): δ 1.63–1.77(bd, 4H), 2.32(s, 3H), 2.65(m, 4H), 2.88(t, 2H), 3.85(t, 2H), 4.80(s, 2H), 7.09–7.32 (m, 7H), 7.72(m, 1H), 9.67(s, 1H), 13.43(bd, 1H).

EXAMPLE 52

Synthesis of 6-methyl-2-(2-methyl-4-fluorophenylamino)-4-(7-methyl-4,5,6,7-tetrahydrothieno[2,3-c]pyridin-6-yl)pyrimidine hydrochloride Step 1: 6-Methyl-4-(7-methyl-4,5,6,7-tetrahydrothieno[2,3-c]pyridin-6-yl)-2-chloropyrimidine In accordance with the same procedure as in Step 1 of Example 1, except that 2,4-dichloro-6-methylpyrimidine (3.1 g, 19 mmol) and 7-methyl-4,5,6,7-tetrahydrothieno[2,3-c]pyridine (2.9 g, 19 mmol) in Preparation 1 were used as starting materials, 2.2 g of the titled compound was obtained as white crystal. (Yield: 41%)

Step 2: 6-Methyl-2-(2-methyl-4-fluorophenylamino)-4-(7-methyl-4,5,6,7-tetrahydrothieno[2,3-c]pyridin-6-yl) pyrimidine hydrochloride After 4-fluoro-2-methylaniline(0.5 ml, 4.6 mmol) was added to a mixture solution of 6-methyl-4-(7-methyl-4,5,6,7-tetrahydrothieno[2,3-c]pyridin-6-yl)-2-chloropyrimidine (0.7 g, 2.5 mmol) and dimethylformamide(10 ml), 0.45 g of the titled compound was obtained in accordance with the same procedure as in Step 2 of Example 1.
Yield: 44.4%
M.P.: 120°–121° C.
$^1$H-NMR(CDCl$_3$): δ 1.54(dd, 3H), 2.40(s, 3H), 2.48(s, 3H), 2.68(m, 1H), 2.80(m, 1H), 3.30(mm, 1H), 4.45(dd, 1H), 5.48(qq, 1H), 6.02(d, 1H), 6.78(m, 1H), 6.95(m, 2H), 7.20(t, 1H), 7.50(m, 1H), 9.80(s, 1H), 14.20(bs, 1H).

EXAMPLE 53

Synthesis of 6-methyl-4-(7-methyl-4,5,6,7-tetrahydrothieno[2,3-c]pyridin-6-yl)-2-(4-fluorophenylamino)pyrimidine hydrochloride After 4-fluoroaniline(0.4 ml, 3.7 mmol) was added to a mixture solution of 6-methyl-4-(7-methyl-4,5,6,7-tetrahydrothieno[2,3-c]pyridin-6-yl)-2-chloropyrimidine (0.7 g, 2.5 mmol) and dimethylformamide(10 ml), 0.7 g of the titled compound was obtained in accordance with the same procedure as in Step 2 of Example 1.
Yield: 71.6%
M.P.: 210°–212° C.
$^1$H-NMR(CDCl$_3$): δ 1.80(dd, 3H), 2.42(s, 3H), 2.80(m, 2H), 3.40(mm, 1H), 4.60(dd, 1H), 5.60(mm, 1H), 6.08(d, 1H), 6.80(m, 1H), 7.08(t, 2H), 7.21(m, 1H), 7.55(m, 2H), 10.40(s, 1H), 13.80(s, 1H).

EXAMPLE 54

Synthesis of 6-methyl-2-(N-methylphenylamino)-4-(7-methyl-4,5,6,7-tetrahydrothieno[2,3-c]pyridin-6-yl)pyrimidine hydrochloride After N-methylaniline(0.45 ml, 4.05 mmol) was added to a mixture solution of 6-methyl-4-(7-methyl-4,5,6,7-tetrahydrothieno[2,3-c]pyridin-6-yl)-2-chloropyrimidine (0.75 g, 2.7 mmol) and dimethylformamide(10 ml), 0.52 g of the titled compound was obtained in accordance with the same procedure as in Step 2 of Example 1.
Yield: 49.7%
M.P.: 175°–178° C.
$^1$H-NMR(CDCl$_3$): δ 1.38(dd, 3H), 2.50(bs, 1H), 2.68–3.05 (m, 4H), 3.45(m, 1H), 3.90(s, 3H), 4.27(dd, 1H), 5.30(qq, 1H), 6.02(d, 1H), 6.78(d, 1H), 7.10–7.35(m, 4H), 7.38–7.55 (m, 2H), 13.50 (bs, 1H).

EXAMPLE 55

Synthesis of 5,6-dimethyl-2-(2-methyl-4-fluorophenylamino)-4-(7-methyl-4,5,6,7-tetrahydrothieno[2,3-c]pyridin-6-yl)pyrimidine hydrochloride Step 1: 5,6-Dimethyl-4-(7-methyl-4,5,6,7-tetrahydrothieno[2,3-c]pyridin-6-yl)-2-chloropyrimidine In accordance with the same procedure as in Step 1 of Example 1, except that N,N-dimethylformamide(20 ml), 5,6-dimethyl-2,4-dichloropyrimidine(2.8 g, 16 mmol) prepared in Step 1 of Example 12 and 7-methyl-4,5,6,7-tetrahydrothieno[2,3-c]pyridine (2.7 g, 17.6 mmol) in Preparation 2 were used as starting materials, 1.85 g of the titled compound was prepared. (Yield: 39.4%)

Step 2: 5,6-Dimethyl-2-(2-methyl-4-fluorophenylamino)-4-(7-methyl-4,5,6,7-tetrahydrothieno[2,3-c]pyridin-6-yl) pyrimidine hydrochloride After 4-fluoro-2-methylaniline(0.5 ml, 4.6 mmol) was added to a mixture solution of 5,6-dimethyl-4-(7-methyl-4,5,6,7-tetrahydrothieno[2,3-c]pyridin-6-yl)-2-chloropyrimidine(0.68 g, 2.3 mmol) and dimethylformamide(5 ml), 0.12 g of the titled compound was obtained in accordance with the same procedure as in Step 2 of Example 1.
Yield: 12.4%
M.P.: >240° C.
$^1$H-NMR(CDCl$_3$): δ 1.60(d, 3H), 2.22(s, 3H), 2.43(s, 3H), 2.55(s, 1H), 2.72(bd, 1H), 2.80(m, 1H), 3.48(m, 1H), 4.30 (m, 1H), 5.58(q, 1H), 6.76(d, 1H), 6.90(m, 2H), 7.18(d, 1H), 7.44(m, 1H), 9.55(s, 1H), 14.36(s, 1H).

EXAMPLE 56

Synthesis of 5-methyl-2-(2-methyl-4-fluorophenylamino)-4-(7-methyl-4,5,6,7-tetrahydrothieno[2,3-c]pyridin-6-yl)-6-ethylpyrimidine hydrochloride Step 1: 5-Methyl-4-(7-methyl-4,5,6,7-tetrahydrothieno[2,3-c]-pyridin-6-yl)-6-ethyl-2-chloropyrimidine In accordance with the same procedure as in Step 1 of Example 1, except that triethylamine(2.2 ml), N,N-dimethyl formamide(20 ml), 2,4-dichloro-5-methyl-6-ethylpyrimidine (2.7 g, 14.1 mmol) prepared in Preparation 4 and 7-methyl-4,5,6,7-tetrahydrothieno[2,3-c]pyridine(2.4 g, 15.7 mmol) prepared in Preparation 1 were used as starting materials, 2.23 g of the titled compound was prepared. (Yield: 51.3%)

Step 2: 5-Methyl-2-(2-methyl-4-fluorophenylamino)-4-(7-methyl-4,5,6,7-tetrahydrothieno[2,3-c]pyridin-6-yl)-6-ethylpyrimidine hydrochloride After 4-fluoro-2-methylaniline(0.51 ml, 4.59 mmol) was added to a mixture solution of 5-methyl-4-(7-methyl-4,5,6,7-tetrahydrothieno[2,3-c]pyridin-6-yl)-6-ethyl-2-chloropyrimidine(0.74 g, 2.4 mmol) and dimethylformamide(5 ml), 0.15 g of the titled compound was obtained in accordance with the same procedure as in Step 2 of Example 1.
Yield: 14.4%
M.P.: 178°–180° C.
$^1$H-NMR(DMSO-d$_6$+TFA): δ 1.07(t, 3H), 1.75(d, 3H), 1.95 (s, 3H), 2.21(s, 3H), 2.35(m, 2H), 2.61(q, 2H), 3.34(m, 2H), 5.05(m, 1H), 6.81(d, 1H), 6.83–7.20(m, 3H), 7.50(d, 1H).

EXAMPLE 57

Synthesis of 6-methyl-4-(2-methyl-4-fluorophenylamino)-2-(1-methyl-1,2,3,4-tetrahydroisoquinolin-2-yl)pyrimidine hydrochloride Step 1: 6-Methyl-2-chloro-4-hydroxypyrimidine To a mixture solution of 6-methyl-2,4-dichloropyrimidine (25 g, 0.153 mol) in tetrahydrofurane(170 ml) was added 1N-NaOH solution(420 ml) and stirred for 48 hours at room temperature. The reaction mixture was washed with ethyl ether to remove impurities, acidified with hydrochloric acid, and then extracted with ethyl acetate. The ethyl acetate layer was dried over anhydrous sodium sulfate, concentrated under reduced pressure to give 13.5 g of titled compound as yellow solid form. (Yield: 66.7%)

Step 2: 6-Methyl-2-(1-methyl-1,2,3,4-tetrahydroisoquinolin-2-yl)-4-hydroxypyrimidine A mixture solution of 6-methyl-2-chloro-4-hydroxypyrimidine(6 g, 37.5 mmol) prepared in the above Step 1, 1-methyl-1,2,3,4-tetrahydroisoquinoline(11.6 g, 78.8 mmol) and N,N-dimethylformamide(30 ml) was stirred at 120 for 2 hours and cooled to give a solid. The resulting solid was dissolved in a mixture solution of dichloromethane and methanol and the undissolved materials were filtered off. The filtrate residue was washed many times with water, dried over anhydrous sodium sulfate, concentrated under reduced pressure to give 7.1 g of titled compound. (Yield: 74.1%)

Step 3: 6-Methyl-2-(1-methyl-1,2,3,4-tetrahydroisoquinolin-2-yl)-4-chloropyrimidine A mixture solution of 6-methyl-2-(1-methyl-1,2,3,4-tetrahydroisoquinolin-2-yl)-4-hydroxypyrimidine(7.0 g, 27.4 mmol) prepared in the above Step 2, phosphorous oxychloride(30 ml) and N,N-dimethylaniline(2, 3 ml) was stirred at 90° C. for 2 hours and cooled. The reaction mixture was added to ice water and basified with sodium bicarbonate and then was extracted with ethyl ether. The ethyl ether layer was dried over anhydrous sodium sulfate, and concentrated under reduced pressure to give 4.5 g of titled compound. (Yield: 60%)

Step 4: 6-Methyl-4-(2-methyl-4-fluorophenylamino)-2-(1-methyl-1,2,3,4-tetrahydroisoquinolin-2-yl)pyrimidine hydrochloride 2-Methyl-4-fluoroaniline(1.1 ml, 10.2 mmol) was added to a mixture solution of 6-methyl-2-(1-methyl-1,2,3,4-tetrahydroisoquinolin-2-yl)-4-chloropyrimidine(1.5 g, 5.5 mmol) and dimethylformamide(10 ml). The reaction solution was stirred for 3 hours and cooled to room temperature. The reaction mixture was diluted with dichloromethane and washed with water. Dichloromethane layer was separated, basified with aqueous sodium hydroxide solution, washed with water, and dried and concentrated in vacuo. The resulting residue was purified with silica gel column chromatography to give a free base form of titled compound as an oily form. The free base form of titled compound was dissolved in ethyl ether, then hydrochloric acid was added thereto. The resulting solid was filtered, dried under reduced pressure to give 0.9 g of titled compound.
Yield: 41%
M.P.: 157°–160° C.
$^1$H-NMR(DMSO-d$_6$): δ 1.42(bs, 3H), 2.25(s, 3H), 2.40(s, 3H), 2.90(bs, 2H), 3.55(bs, 1H), 4.40(bs, 1H), 5.60(bs, 1H), 6.40(s, 1H), 7.00–7.30(m, 6H), 7.40(bs, 1H), 10.60(bs, 1H), 12.35(bs, 1H).

EXAMPLE 58

Synthesis of 6-methyl-4-(4-fluorophenylamino)-2-(1-methyl-1,2,3,4-tetrahydroisoquinolin-2-yl) pyrimidine hydrochloride After 4-fluoroaniline(0.8 ml, 8.4 mmol) was added to a mixture solution of 6-methyl-2-(1-methyl-1,2,3,4-tetrahydroisoquinolin-2-yl)-4-chloropyrimidine(1.5 g, 5.5 mmol) and dimethylformamide(10 ml), 1.1 g of the titled compound was obtained in accordance with the same procedure as in Step 4 of Example 57.
Yield: 52%
M.P.: 165°–167° C.
$^1$H-NMR(DMSO-d$_6$): δ 1.58(d, 3H), 2.50(s, 3H), 3.00(bs, 2H), 3.60(bs, 1H), 4.50(bs, 1H), 5.75(bs, 1H), 6.38(bs, 1H), 7.00–7.50(m, 6H), 7.75(bs, 2H), 11.20(bs, 1H), 12.38(bs, 1H).

EXAMPLE 59

Synthesis of 6-methyl-4-(2-methyl-4-fluorophenylamino)-2-(7-methyl-4,5,6,7-tetrahydrothieno[2,3-c]pyridin-6-yl)pyrimidine hydrochloride Step 1: 6-Methyl-2-(7-methyl-4,5,6,7-tetrahydrothieno[2,3-c]pyridin-6-yl)-4-hydroxypyrimidine In accordance with the same procedure as in Step 2 of Example 57, except that 6-methyl-2-chloro-4-hydroxypyrimidine(6 g, 37.5 mmol) prepared in Step 1 of Example 57, and 7-methyl-4,5,6,7-tetrahydrothieno[2,3-c]pyridine (12.07 g, 78.75 mmol) prepared in preparation 1 were used as starting materials, 6.9 g of the titled compound was prepared.
(Yield: 70%)

Step 2: 6-Methyl-2-(7-methyl-4,5,6,7-tetrahydrothieno[2,3-c]pyridine-6-yl)-4-chloropyrimidine In accordance with the same procedure as in Step 3 of Example 57, except that 6-methyl-2-(7-methyl-4,5,6,7-tetrahydrothieno[2,3-c]pyridin-6-yl)-4-hydroxypyrimidine (6.5 g, 24.9 mmol) prepared in the above Step 1 was used as a starting material, 4.5 g of the titled compound was prepared.
(Yield: 70%)

Step 3: 6-Methyl-4-(2-methyl-4-fluorophenylamino)-2-(7-methyl-4,5,6,7-tetrahydrothieno[2,3-c]pyridin-6-yl) pyrimidine hydrochloride After 2-methyl-4-fluoroaniline(0.38 ml, 3.42 mmol) was added to a mixture solution of 6-methyl-2-(7-methyl-4,5,6, 7-tetrahydrothieno[2,3-c]pyridin-6-yl)-4-chloropyrimidine (0.5 g, 1.8 mmol) and dimethylformamide(10 ml), 0.35 g of the titled compound was obtained in accordance with the same procedure as in Step 4 of Example 57.
Yield: 48%
M.P.: 135°–137° C.
$^1$H-NMR(CDCl$_3$): δ 1.43(bs, 3H), 2.22(s, 3H), 2.42(s, 3H), 2.70(bs, 2H), 3.36(bs, 1H), 4.65(m, 1H), 5.70(m, 1H), 6.38(bs, 1H), 6.85(d, 1H), 7.04–7.30(m, 2H), 7.34–7.50(m, 2H), 10.58(bs, 1H), 12.42(bs, 1H).

EXAMPLE 60

Synthesis of 6-methyl-4-(4-fluorophenylamino)-2-(7-methyl-4,5,6,7-tetrahydrothieno[2,3-c]pyridin-6-yl)pyrimidine hydrochloride After 4-fluoroaniline(0.26 ml, 2.74 mmol) was added to a mixture solution of 6-methyl-2-(7-methyl-4,5,6,7-tetrahydrothieno[2,3-c]pyridin-6-yl)-4-chloropyrimidine (0.5 g, 1.8 mmol) and dimethylformamide(10 ml), 0.30 g of the titled compound was obtained in accordance with the same procedure as in Step 4 of Example 57.
Yield: 42.6%
M.P.: 245°–247° C.
$^1$H-NMR(DMSO-d$_6$): δ 1.58(d, 3H), 2.42(s, 3H), 2.81(m, 2H), 3.48(m, 1H), 4.64(m, 1H), 5.75(m, 1H), 6.25(s, 1H), 6.90(d, 1H), 7.30(t, 3H), 7.42(d, 2H), 7.70(m, 2H).

EXAMPLE 61

Synthesis of 6-ethyl-2-(2-methyl-4-fluorophenylamino)-4-(1-methyl-1,2,3,4-tetrahydroisoquinolin-2-yl)pyrimidine hydrochloride
Step 1: 6-ethyl-2-chloro-4-hydroxypyrimidine In accordance with the same procedure as in Step 1 of Example 57, except that 6-ethyl-2,4-dichloropyrimidine (27.08 g, 0.153 mol) prepared in Preparation 2 was used as a starting material, 14.6 g of the titled compound was prepared. (Yield: 66.7%)

Step 2: 6-Ethyl-2-(1-methyl-1,2,3,4-tetrahydroisoquinolin-2-yl)-4-hydroxypyrimidine In accordance with the same procedure as in Step 2 of Example 57, except that 6-ethyl-2-chloro-4-hydroxypyrimidine (7.0 g, 37.5 mmol) prepared in the above Step 1 and 1-methyl-1,2,3,4-tetrahydroisoquinoline(11.04 g, 75 mmol) were used as starting materials, 8.1 g of the titled compound was prepared. (Yield: 80%)

Step 3: 6-Ethyl-2-(1-methyl-1,2,3,4-tetrahydroisoquinolin-2-yl)-4-chloropyrimidine In accordance with the same procedure as in Step 3 of Example 57, except that 6-ethyl-2-(1-methyl-1,2,3,4-tetrahydroisoquinolin-2-yl)-4-hydroxypyrimidine(8.0 g, 29.7 mmol) prepared in the above Step 2 was used as a starting material, 4.9 g of the titled compound was prepared. (Yield: 57.3%)

Step 4: 6-Ethyl-4-(2-methyl-4-fluorophenylamino)-2-(1-methyl-1,2,3,4-tetrahydroisoquinolin-2-yl)pyrimidine hydrochloride After 2-methyl-4-fluoroaniline(1.1 ml, 10.2 mmol) was added to a mixture solution of 6-ethyl-2-(1-methyl-1,2,3,4-tetrahydroisoquinolin-2-yl)-4-chloropyrimidine(2.0 g, 7.0 mmol) and dimethylformamide(10 ml), 1.1 g of the titled compound was obtained in accordance with the same procedure as in Step 4 of Example 57.

Yield: 38%

M.P.: 123°–125° C.

$^1$H-NMR(DMSO-d$_6$): δ 1.16–1.57(m, 6H), 2.27(s, 3H), 2.77–2.94 (m, 4H), 3.50(bs, 1H), 4.40(bs, 1H), 5.63(bs, 1H), 6.45(s, 1H), 7.08–7.52(m, 7H), 10.61(s, 1H), 12.27(s, 1H).

EXAMPLE 62

Synthesis of 6-ethyl-4-(2-methyl-4-fluorophenylamino)-2-(1,2,3,4-tetrahydroisoquinolin-2-yl)pyrimidine hydrochloride Step 1: 6-Ethyl-2-(1,2,3,4-tetrahydroisoquinolin-2-yl)-4-hydroxypyrimidine In accordance with the same procedure as in Step 2 of Example 57, except that 6-ethyl-2-chloro-4-hydroxypyrimidine(7.0 g, 37.5 mmol) prepared in Step 1 of Example 59 and 1,2,3,4-tetrahydroisoquinoline(9.4 ml, 75 mmol) were used as starting materials, 8.1 g of the titled compound was prepared. (Yield: 84.6%)

Step 2: 6-Ethyl-2-(1,2,3,4-tetrahydroisoquinolin-2-yl)-4-chloropyrimidine

In accordance with the same procedure as in Step 2 of Example 57, except that 6-ethyl-2-(1,2,3,4-tetrahydroisoquinoline-2-yl)-4-hydroxypyrimidine(8.0 g, 31.3 mmol) prepared in the above Step 1 was used as a starting material, 4.7 g of the titled compound was prepared. (Yield: 55%)

Step 3: 6-Ethyl-4-(2-methyl-4-fluorophenylamino)-2-(1,2,3,4-tetrahydroisoquinolin-2-yl)pyrimidine hydrochloride After 2-methyl-4-fluoroaniline(0.35 ml, 3.15 mmol) was added to a mixture solution of 6-ethyl-2-(1,2,3,4-tetrahydroisoquinolin-2-yl)-4-chloropyrimidine(0.40 g, 1.46 mmol) and dimethylformamide(10 ml), 0.51 g of the titled compound was obtained in accordance with the same procedure as in Step 4 of Example 57.

Yield: 88%

M.P.: 122°–124° C.

$^1$H-NMR(DMSO-d$_6$): δ 1.30(q, 3H), 2.24(s, 3H), 2.74–2.95 (m, 4H), 3.88(t, 2H), 4.83(s, 2H), 6.44(s, 1H), 7.05–7.55(m, 7H), 10.62(s, 1H), 12.30(s, 1H).

EXAMPLE 63

Synthesis of 6-ethyl-4-(4-fluorophenylamino)-2-(1,2,3,4-tetrahydroisoquinolin-2-yl)pyrimidine hydrochloride After 4-fluoroaniline(0.30 ml, 3.17 mmol) was added to a mixture solution of 6-ethyl-2-(1,2,3,4-tetrahydroisoquinolin-2-yl)-4-chloropyrimidine(0.40 g, 1.46 mmol) and dimethylformamide(10 ml), 0.44 g of the titled compound was obtained in accordance with the same procedure as in Step 4 of Example 57.

Yield: 78%

M.P.: 124°–126° C.

$^1$H-NMR(CDCl$_3$): δ 1.41(q, 3H), 2.70–2.95(m, 4H), 4.05 (bs, 2H), 4.95(s, 2H), 6.16(s, 1H), 6.35–6.80(t, 2H), 7.04–7.14(m, 4H), 7.66–7.75(dd, 2H), 11.05(s, 1H), 12.06(s, 1H).

EXAMPLE 64

Synthesis of 6-ethyl-4-(N-methylphenylamino)-2-(1,2,3,4-tetrahydroisoquinolin-2-yl)pyrimidine hydrochloride After N-methylaniline(0.10 ml, 9.22 mmol) was added to a mixture solution of 6-ethyl-2-(1,2,3,4-tetrahydroisoquinolin-2-yl)-4-chloropyrimidine(1.20 g, 4.38 mmol) and dimethylformamide(10 ml), 0.22 g of the titled compound was obtained in accordance with the same procedure as in Step 4 of Example 57.

Yield: 13%

M.P.: 130°–132° C.

$^1$H-NMR(CDCl$_3$): δ 1.15(t, 3H), 2.97–3.15(m, 4H), 3.55(s, 3H), 4.38(bs, 2H), 5.10(bs, 2H), 5.50(s, 1H), 7.10–7.40(m, 6H), 7.50–7.60(m, 3H), 13.40(s, 1H).

EXAMPLE 65

Synthesis of 5,6-dimethyl-4-(2-methyl-4-fluorophenylamino)-2-(1-methyl-1,2,3,4-tetrahydroisoquinolin-2-yl)pyrimidine hydrochloride Step 1: 5,6-Dimethyl-2,4-dichloropyrimidine A mixture solution of 5,6-dimethyl-2,4-dihydroxypyrimidine(72 g, 0.51 mol), phosphorous oxychloride(250 ml) and N,N-dimethylaniline(41 ml) was heated to reflux for 3 hours and cooled to room temperature. The reaction mixture was added to ice water and the resulting solid was filtered and recrystallized from dichloromethane to give 58.5 g of the titled compound. (Yield: 64.7%)

Step 2: 5,6-Dimethyl-2-chloro-4-hydroxypyrimidine

In accordance with the same procedure as in Step 1 of Example 57, except that 5,6-dimethyl-2,4-dichloropyrimidine (50.0 g, 0.28 mol) prepared in the above Step 1 was used as a starting material, 24.4 g of the titled compound was prepared. (Yield: 55%)

Step 3: 5,6-Dimethyl-2-(1-methyl-1,2,3,4-tetrahydroisoquinolin-2-yl)-4-hydroxypyrimidine In accordance with the same procedure as in Step 2 of Example 57, except that 5,6-dimethyl-2-chloro-4-hydroxypyrimidine(6.0 g, 37.8 mmol) prepared in the above Step 2 was used as a starting material, 7.6 g of the titled compound was prepared. (Yield: 75%)

Step 4: 5,6-Dimethyl-2-(1-methyl-1,2,3,4-tetrahydroisoquinolin-2-yl)-4-chloropyrimidine In accordance with the same procedure as in Step 3 of Example 57, except that 5,6-dimethyl-2-(1-methyl-1,2,3,4-tetrahydroisoquinolin-2-yl)-4-hydroxypyrimidine(7.0 g, 26 mmol) prepared in the above Step 3 was used as starting material, 3.9 g of the titled compound was prepared. (Yield: 52%)

Step 5: 5,6-Dimethyl-4-(2-methyl-4-fluorophenylamino)-2-(1-methyl-1,2,3,4-tetrahydroisoquinolin-2-yl)pyrimidine hydrochloride After 2-methyl-4-fluoroaniline(0.7 ml, 6.3 mmol) was added to a mixture solution of 5,6-dimethyl-2-(1-methyl-1, 2,3,4-tetrahydroisoquinolin-2-yl)-4-chloropyrimidine(0.85 g, 3.0 mmol) and dimethylformamide(10 ml), 0.9 g of the titled compound was obtained in accordance with the same procedure as in Step 4 of Example 57.
Yield: 72.6%
M.P.: 208°–211° C.
$^1$H-NMR(DMSO-$d_6$): δ 1.28(d, 3H), 2.16(s, 3H), 2.18(s, 3H), 2.55(s, 3H), 2.80(bd, 2H), 3.42(bd, 1H), 4.34(bd, 1H), 5.44(bd, 1H), 7.02(bd, 1H), 7.24(m, 6H), 9.65(s, 1H), 12.30 (bd, 1H).

EXAMPLE 66

Synthesis of (R)-5,6-dimethyl-4-(2-methyl-4-fluorophenylamino)-2-(1-methyl-1,2,3,4-tetrahydroisoquinolin-2-yl)pyrimidine hydrochloride Step 1: (R)-5,6-Dimethyl-2-(1-methyl-1,2,3,4-tetrahydroisoquinoline-2-yl)-4-hydroxypyrimidine In accordance with the same procedure as in Step 2 of Example 57, except that 5,6-dimethyl-2-chloro-4-hydroxypyrimidine(6.0 g, 37.8 mmol) prepared in Example 60 and (R)-1-methyl-1,2,3,4-tetrahydroisoquinoline(11.7 g, 79.5 mmol) were used as starting materials, 7.0 g of the titled compound was prepared. (Yield: 68.8%)

Step 2: (R)-5,6-Dimethyl-2-(1-methyl-1,2,3,4-tetrahydroisoquinolin-2-yl)-4-chloropyrimidine In accordance with the same procedure as in Step 3 of Example 57, except that (R)-5,6-dimethyl-2-(1-methyl-1,2,3,4-tetrahydroisoquinolin-2-yl)-4-hydroxypyrimidine (7.0 g, 26 mmol) prepared in the above Step 1 was used as a starting material, 3.2 g of the titled compound was prepared. (Yield: 42.8%)

Step 3: (R)-5,6-Dimethyl-4-(2-methyl-4-fluorophenylamino)-2-(1-methyl-1,2,3,4-tetrahydroisoquinolin-2-yl)pyrimidine hydrochloride After 2-methyl-4-fluoroaniline(0.82 ml, 7.35 mmol) was added to a mixture solution of (R)-5,6-dimethyl-2-(1-methyl-1,2,3,4-tetrahydroisoquinolin-2-yl)-4-chloropyrimidine(1.0 g, 3.5 mmol) prepared in the above Step 2 and dimethylformamide (10 ml), 1.2 g of the titled compound was obtained in accordance with the same procedure as in Step 4 of Example 57.
Yield: 83%
M.P.: 207°–209° C.
$^1$H-NMR(DMSO-$d_6$): δ 1.28(d, 3H), 2.16(s, 3H), 2.18(s, 3H), 2.55(s, 3H), 2.80(bd, 2H), 3.42(bd, 1H), 4.34(bd, 1H), 5.44(bd, 1H), 7.02(bd, 1H), 7.24(m, 6H), 9.65(s, 1H), 12.30 (bd, 1H).

EXAMPLE 67

Synthesis of (S)-5,6-dimethyl-4-(2-methyl-4-fluorophenylamino)-2-(1-methyl-1,2,3,4-tetrahydroisoquinolin-2-yl)pyrimidine hydrochloride Step 1: (S)-5,6-Dimethyl-2-(1-methyl-1,2,3,4-tetrahydroisoquinolin-2-yl)-4-hydroxypyrimidine In accordance with the same procedure as in Step 2 of Example 57, except that 5,6-dimethyl-2-chloro-4-hydroxypyrimidine(6.0 g, 37.8 mmol) prepared in Example 60 and (S)-1-methyl-1,2,3,4-tetrahydroisoquinoline(11.7 g, 79.5 mmol) were used as starting materials, 6.6 g of the titled compound was prepared. (Yield: 64.8%)

Step 2: (S)-5,6-Dimethyl-2-(1-methyl-1,2,3,4-tetrahydroisoquinolin-2-yl)-4-chloropyrimidine In accordance with the same procedure as in Step 2 of Example 57, except that (S)-5,6-dimethyl-2-(1-methyl-1,2,3,4-tetrahydroisoquinolin-2-yl)-4-hydroxypyrimidine (7.0 g, 26 mmol) prepared in the above Step 1 was used as a starting material, 3.5 g of the titled compound was prepared.

(Yield: 46.8%)

Step 3: (S)-5,6-Dimethyl-4-(2-methyl-4-fluorophenylamino)-2-(1-methyl-1,2,3,4-tetrahydroisoquinolin-2-yl)pyrimidine hydrochloride After 2-methyl-4-fluoroaniline(0.82 ml, 7.35 mmol) was added to a mixture solution of (S)-5,6-dimethyl-2-(1-methyl-1,2,3,4-tetrahydroisoquinolin-2-yl)-4-chloropyrimidine(1.0 g, 3.5 mmol) obtained in the above Step 2 and dimethylformamide (10 ml), 1.0 g of the titled compound was obtained in accordance with the same procedure as in Step 4 of Example 57.
Yield: 69.2%
M.P.: 208°–210° C.
$^1$H-NMR(DMSO-$d_6$): δ 1.28(d, 3H), 2.16(s, 3H), 2.18(s, 3H), 2.55(s, 3H), 2.80(bd, 2H), 3.42(bd, 1H), 4.34(bd, 1H), 5.44(bd, 1H), 7.02(bd, 1H), 7.24(m, 6H), 9.65(s, 1H), 12.30 (bd, 1H).

EXAMPLE 68

Synthesis of 5,6-dimethyl-4-(4-fluorophenylamino)-2-(1-methyl-1,2,3,4-tetrahydroisoquinolin-2-yl)pyrimidine hydrochloride After 4-fluoroaniline(0.6 ml, 6.3 mmol) was added to a mixture solution of 5,6-dimethyl-2-(1-methyl-1,2,3,4-tetrahydroisoquinolin-2-yl)-4-chloropyrimidine(0.85 g, 3.0 mmol) and dimethylformamide(10 ml), 0.62 g of the titled compound was obtained in accordance with the same procedure as in Step 4 of Example 57.
Yield: 52%
M.P.: 246°–250° C.
$^1$H-NMR(DMSO-$d_6$): δ 1.40(d, 3H), 2.18(s, 3H), 2.50(s, 3H), 2.88(bd, 2H), 3.42(bd, 1H), 4.42(bd, 1H), 5.62(bd, 1H), 7.18(m, 4H), 7.30(t, 2H), 7.63(q, 2H), 9.70(s, 1H), 12.30(bd, 1H).

EXAMPLE 69

Synthesis of (R)-5,6-dimethyl-4-(4-fluorophenylamino)-2-(1-methyl-1,2,3,4-tetrahydroisoquinolin-2-yl)pyrimidine hydrochloride After 4-fluoroaniline(0.6 ml, 6.3 mmol) was added to a mixture solution of (R)-5,6-dimethyl-2-(1-methyl-1,2,3,4-tetrahydroisoquinolin-2-yl)-4-chloropyrimidine(0.85 g, 3.0 mmol) prepared in Step 2 of Example 61 and dimethylformamide(10 ml), 0.50 g of the titled compound was obtained in accordance with the same procedure as in Step 4 of Example 57.
Yield: 41.8%
M.P.: 245°–248° C.
$^1$H-NMR(DMSO-$d_6$): δ 1.40(d, 3H), 2.18(s, 3H), 2.50(s, 3H), 2.88(bd, 2H), 3.42(bd, 1H), 4.42(bd, 1H), 5.62(bd, 1H), 7.18(m, 4H), 7.30(t, 2H), 7.63(q, 2H), 9.70(s, 1H), 12.30(bd, 1H).

EXAMPLE 70

Synthesis of (S)-5,6-dimethyl-4-(4-fluorophenylamino)-2-(1-methyl-1,2,3,4-tetrahydroisoquinolin-2-yl)pyrimidine hydrochloride After 4-fluoroaniline(0.6 ml, 6.3 mmol) was added to mixture solution of (S)-5,6-dimethyl-2-(1-methyl-1,2,3,4-tetrahydroisoquinoline-2-yl)-4-chloropyrimidine(0.85 g, 3.0 mmol) prepared in Step 2 of Example 62 and dimethylformamide (10 ml), 0.55 g of the titled compound was obtained in accordance with the same procedure as in Step 4 of Example 57.

Yield: 46%
M.P.: 245°–247° C.
$^1$H-NMR(DMSO-d$_6$): δ 1.40(d, 3H), 2.18(s, 3H), 2.50(s, 3H), 2.88(bd, 2H), 3.42(bd, 1H), 4.42(bd, 1H), 5.62(bd, 1H), 7.18(m, 4H), 7.30(t, 2H), 7.63(q, 2H), 9.70(s, 1H), 12.30(bd, 1H).

EXAMPLE 71

Synthesis of 5,6-dimethyl-4-(N-methylphenylamino)-2-(1-methyl-1,2,3,4-tetrahydroisoquinolin-2-yl)pyrimidine hydrochloride After N-methylaniline(0.6 ml, 5 mmol) was added to a mixture solution of 5,6-dimethyl-2-(1-methyl-1,2,3,4-tetrahydroisoquinolin-2-yl)-4-chloropyrimidine(0.7 g, 2.4 mmol) and dimethylformamide(10 ml), 0.45 g of the titled compound was obtained in accordance with the same procedure as in Step 4 of Example 57.
Yield: 47%
M.P.: 91°–95° C.
$^1$H-NMR(CDCl$_3$): δ 1.32(s, 3H), 1.64(d, 3H), 1.90(bd, 1H), 2.72(s, 3H), 3.02(bd, 1H), 3.25(bd, 1H), 3.56(s, 3H), 3.70 (bd, 1H), 5.05(bs, 1H), 5.78(bs, 1H), 7.20(m, 6H), 7.42(m, 3H), 13.44(s, 1H).

EXAMPLE 72

Synthesis of (R)-5,6-dimethyl-4-(N-methylphenylamino)-2-(1-methyl-1,2,3,4-tetrahydroisoquinolin-2-yl)pyrimidine hydrochloride After N-methylaniline(0.6 ml, 5 mmol) was added to a mixture solution of (R)-5,6-dimethyl-2-(1-methyl-1,2,3,4-tetrahydroisoquinolin-2-yl)-2-chloropyrimidine(0.7 g, 2.4 mmol) prepared in the Step 2 of Example 61 and dimethylformamide(10 ml), 0.50 g of the titled compound was obtained in accordance with the same procedure as in Step 4 of Example 57.
Yield: 52.7%
M.P.: 90°–93° C.
$^1$H-NMR(CDCl$_3$): δ 1.32(s, 3H), 1.64(d, 3H), 1.90(bd, 1H), 2.72(s, 3H), 3.02(bd, 1H), 3.25(bd, 1H), 3.56(s, 3H), 3.70 (bd, 1H), 5.05(bs, 1H), 5.78(bs, 1H), 7.20(m, 6H), 7.42(m, 3H), 13.44(s, 1H).

EXAMPLE 73

Synthesis of (S)-5,6-dimethyl-4-(N-methylphenylamino)-2-(1-methyl-1,2,3,4-tetrahydroisoquinolin-2-yl)pyrimidine hydrochloride After N-methylaniline(0.6 ml, 5 mmol) was added to a mixture solution of (S)-5,6-dimethyl-2-(1-methyl-1,2,3,4-tetrahydroisoquinolin-2-yl)-4-chloropyrimidine(0.7 g, 2.4 mmol) prepared in the Step 2 of Example 62 and dimethylformamide(10 ml), 0.42 g of the titled compound was obtained in accordance with the same procedure as in Step 4 of Example 57.
Yield: 44.4%
M.P.: 91°–94° C.
$^1$H-NMR(CDCl$_3$): δ 1.32(s, 3H), 1.64(d, 3H), 1.90(bd, 1H), 2.72(s, 3H), 3.02(bd, 1H), 3.25(bd, 1H), 3.56(s, 3H), 3.70 (bd, 1H), 5.05(bs, 1H), 5.78(bs, 1H), 7.20(m, 6H), 7.42(m, 3H), 13.44(s, 1H).

EXAMPLE 74

Synthesis of 5,6-dimethyl-4-(2-methyl-4-fluorophenylamino)-2-(1,2,3,4-tetrahydroisoquinolin-2-yl)pyrimidine hydrochloride
Step 1: 5,6-Dimethyl-2-(1,2,3,4-tetrahydroisoquinolin-2-yl)-4-hydroxypyrimidine In accordance with the same procedure as in Step 2 of Example 57, except that 5,6-dimethyl-2-chloro-4-hydroxypyrimidine (6.0 g, 37.8 mmol) prepared in the Step 2 of Example 65 and 1,2,3,4-tetrahydroisoquinoline(10 ml, 79.9 mmol) were used as starting materials, 7.8 g of the titled compound was prepared. (Yield: 81%)
Step 2: 5,6-Dimethyl-2-(1,2,3,4-tetrahydroisoquinolin-2-yl)-4-chloropyrimidine In accordance with the same procedure as in Step 3 of Example 57, except that 5,6-dimethyl-2-(1,2,3,4-tetrahydroisoquinolin-2-yl)-4-hydroxypyrimidine(7.0 g, 26 mmol) prepared in the above Step 1 was used as starting materials, 4.1 g of the titled compound was prepared. (Yield: 57.6%)
Step 3: 5,6-Dimethyl-4-(2-methyl-4-fluorophenylamino)-2-(1,2,3,4-tetrahydroisoquinoline-2-yl)pyrimidine hydrochloride After 2-methyl-4-fluoroaniline(0.3 ml, 2.7 mmol) was added to a mixture solution of (5,6-dimethyl-2-(1,2,3,4-tetrahydroisoquinolin-2-yl)-4-chloropyrimidine(0.30 g, 1.0 mmol) and dimethylformamide(10 ml), 0.12 g of the titled compound was obtained in accordance with the same procedure as in Step 4 of Example 57.
Yield: 30%
M.P.: 117°–120° C.
$^1$H-NMR(DMSO-d$_6$): δ 2.13(s, 3H), 2.16(s, 3H), 2.52(s, 3H), 2.81(t, 2H), 3.79(t, 2H), 4.74(s, 2H), 7.00(bd, 1H), 7.09–7.34(m, 6H), 9.16(s, 1H), 12.35(s, 1H).

EXAMPLE 75

Synthesis of 5,6-dimethyl-4-(4-fluorophenylamino)-2-(1,2,3,4-tetrahydroisoquinolin-2-yl)pyrimidine hydrochloride After 4-fluoroaniline(0.24 ml, 2.5 mmol) was added to a mixture solution of 5,6-dimethyl-2-(1,2,3,4-tetrahydroisoquinolin-2-yl)-4-chloropyrimidine(0.33 g, 1.2 mmol) and dimethylformamide(10 ml), 0.31 g of the titled compound was obtained in accordance with the same procedure as in Step 4 of Example 57.
Yield: 67%
M.P.: 128°–130° C.
$^1$H-NMR(DMSO-d$_6$): δ 2.13(s, 3H), 2.53(s, 3H), 2.90(t, 2H), 3.93(t, 2H), 4.86(s, 2H), 7.18–7.34(m, 6H), 7.63(m, 2H), 9.71(s, 1H), 12.20(bd, 1H).

EXAMPLE 76

Synthesis of 5,6-dimethyl-4-(N-methylphenylamino)-2-(1,2,3,4-tetrahydroisoquinolin-2-yl)pyrimidine hydrochloride After N-methylaniline(0.5 ml, 4.2 mmol) was added to a mixture solution of 5,6-dimethyl-2-(1,2,3,4-tetrahydroisoquinolin-2-yl)-4-chloropyrimidine(0.6 g, 2.0 mmol) and dimethylformamide(10 ml), 0.28 g of the titled compound was obtained in accordance with the same procedure as in Step 4 of Example 57.
Yield: 37%
M.P.: 209°–211° C.
$^1$H-NMR(DMSO-d$_6$): δ 1.24(s, 3H), 2.41(s, 3H), 2.98(t, 2H), 3.52(s, 3H), 4.07(t, 2H), 5.02(s, 2H), 7.24–7.45(m, 9H), 12.65(bd, 1H).

EXAMPLE 77

Synthesis of 5,6-dimethyl-4-(2-methyl-4-fluorophenylamino)-2-(7-methyl-4,5,6,7-tetrahydrothieno[2,3-c]pyridin-6-yl)pyrimidine hydrochloride
Step 1: 5,6-Dimethyl-4-(7-methyl-4,5,6,7-tetrahydrothieno[2,3-c]pyridin-6-yl)-2-hydroxypyrimidine In accordance with the same procedure as in Step 2 of Example 57, except that 5,6-dimethyl-2-chloro-4-hydroxypyrimidine(6.0 g, 37.8 mmol) prepared in the Step 2 of Example 65 and 7-methyl-4,5,6,7-tetrahydrothieno[2,3-c]pyridine (12.2 g, 79.6 mmol) prepared in Preparation 1 were used as starting materials, 6.5 g of the titled compound was obtained. (Yield: 62.4%)

Step 2: 5,6-Dimethyl-4-(7-methyl-4,5,6,7-tetrahydrothieno[2,3-c]pyridin-6-yl)-2-chloropyrimidine In accordance with the same procedure as in Step 3 of Example 57, except that 5,6-dimethyl-2-(7-methyl-4,5,6,7-tetrahydrothieno[2,3-c]pyridin-6-yl)-4-hydroxypyrimidine (6.0 g, 21.8 mmol) prepared in the above Step 1 was used as a starting material, 3.5 g of the titled compound was prepared.
(Yield: 54.6%)

Step 3: 5,6-Dimethyl-4-(2-methyl-4-fluorophenylamino)-2-(7-methyl-4,5,6,7-tetrahydrothieno[2,3-c]pyridin-6-yl) pyrimidine hydrochloride After 2-methyl-4-fluoroaniline(0.3 ml, 3 mmol) was added to a mixture solution of 5,6-dimethyl-2-(7-methyl-4,5,6,7-tetrahydrothieno[2,3-c]pyridin-6-yl)-4-chloropyrimidine (0.4 g, 1.4 mmol) and dimethylformamide (10 ml), 0.14 g of the titled compound was obtained in accordance with the same procedure as in Step 4 of Example 57.
Yield: 24%
M.P.: 134°–137° C.
$^1$H-NMR(DMSO-$d_6$): δ 1.35(d, 3H), 2.14(s, 3H), 2.18(s, 3H), 2.42(s, 3H), 2.65(bd, 2H), 3.56(bd, 1H), 4.54(m, 1H), 5.56(bd, 1H), 6.84(d, 1H), 7.15–7.38(m, 3H), 7.41(d, 1H), 9.72(s, 1H), 12.44(bd, 1H).

EXAMPLE 78

Synthesis of 5,6-dimethyl-2-(7-methyl-4,5,6,7-tetrahydrothieno[2,3-c]pyridin-6-yl)-4-(4-fluorophenylamino)pyrimidine hydrochloride After 4-fluoroaniline(0.3 ml, 3 mmol) was added to a mixture solution of 5,6-dimethyl-2-(7-methyl-4,5,6,7-tetrahydrothieno[2,3-c]pyridin-6-yl)-4-chloropyrimidine (0.4 g, 1.4 mmol) and dimethylformamide(10 ml), 0.15 g of the titled compound was obtained in accordance with the same procedure as in Step 4 of Example 57.
Yield: 26.5%
M.P.: 141°–145° C.
$^1$H-NMR(DMSO-$d_6$): δ 1.42(d, 3H), 2.16(s, 3H), 2.52(s, 3H), 2.70(bd, 2H), 3.38(m, 1H), 4.65(bd, 1H), 5.75(bd, 1H), 6.84(d, 1H), 7.30(m, 2H), 7.42(d, 1H), 7.61(m, 2H), 9.80(s, 1H), 12.62(bd, 1H).

EXAMPLE 79

Synthesis of 5,6-dimethyl-4-(N-methylphenylamino)-2-(7-methyl-4,5,6,7-tetrahydrothieno[2,3-c]pyridin-6-yl)pyrimidine hydrochloride After N-methylaniline(0.5 ml, 4 mmol) was added to a mixture solution of 5,6-dimethyl-2-(7-methyl-4,5,6,7-tetrahydrothieno[2,3-c]pyridin-6-yl)-4-chloropyrimidine (0.64 g, 2 mmol) and dimethylformamide(10 ml), 0.16 g of the titled compound was obtained in accordance with the same procedure as in Step 4 of Example 57.
Yield: 20%
M.P.: 117°–120° C.
$^1$H-NMR(CDCl$_3$): δ 1.32(s, 3H), 1.65(d, 3H), 2.72(s, 3H), 2.78(bd, 1H), 3.20(bd, 1H), 3.51(bd, 1H), 3.56(s, 3H), 5.36(bd, 1H), 6.03(bd, 1H), 6.82(d, 1H), 6.88(m, 3H), 7.37–7.48(m, 3H), 14.52(s, 1H).

EXAMPLE 80

Synthesis of 5-methyl-6-ethyl-4-(2-methyl-4-fluorophenylamino)-2-(1-methyl-1,2,3,4-tetrahydroisoquinolin-2-yl)pyrimidine hydrochloride Step 1: 5-Methyl-6-ethyl-2-chloro-4-hydroxypyrimidine In accordance with the same procedure as in Step 1 of Example 57, except that 2,4-dichloro-5-methyl-6-ethylpyrimidine(2.7 g, 14.1 mmol) prepared in Preparation 4 was used as a starting material, 1.8 g of the titled compound was prepared. (Yield: 72%)

Step 2: 5-Methyl-6-ethyl-2-(1-methyl-1,2,3,4-tetrahydroisoquinolin-2-yl)-4-hydroxypyrimidine In accordance with the same procedure as in Step 2 of Example 57, except that 5-methyl-6-ethyl-2-chloro-4-hydroxypyrimidine(1.8 g, 10.1 mmol) prepared in the above Step 1 was used as a starting material, 2.4 g of the titled compound was prepared. (Yield: 84%)

Step 3: 5-Methyl-6-ethyl-2-(1-methyl-1,2,3,4-tetrahydroisoquinolin-2-yl)-4-chloropyrimidine In accordance with the same procedure as in Step 3 of Example 57, except that 5-methyl-6-ethyl-2-(1-methyl-1,2,3,4-tetrahydroisoquinolin-2-yl)-4-hydroxypyrimidine(2.4 g, 8.5 mmol) prepared in the above Step 2 was used as a starting material, 1.6 g of the titled compound was prepared. (Yield: 62.4%)

Step 4: 5-Methyl-6-ethyl-4-(2-methyl-4-fluorophenylamino)-2-(1-methyl-1,2,3,4-tetrahydroisoquinolin-2-yl)pyrimidine hydrochloride After 2-methyl-4-fluoroaniline(0.42 ml, 3.8 mmol) was added to a mixture solution of 5-methyl-6-ethyl-2-(1-methyl-1,2,3,4-tetrahydroisoquinolin-2-yl)-4-chloropyrimidine(0.6 g, 2.0 mmol) and dimethylformamide (10 ml), 0.35 g of the titled compound was obtained in accordance with the same procedure as in Step 4 of Example 57.
Yield: 41%
M.P.: 270°–272° C.
$^1$H-NMR(DMSO-$d_6$): δ 1.22(t, 3H), 1.35(d, 3H), 2.16(s, 3H), 2.20(s, 3H), 2.75–3.00(m, 4H), 3.48(m, 1H), 4.20(m, 1H), 5.38(bs, 1H), 7.00–7.40(m, 7H).

EXAMPLE 81

Synthesis of 4-(2-methyl-4-fluorophenylamino)-2-(1-methyl-1,2,3,4-tetrahydroisoquinolin-2-yl) cyclopenta[d]pyrimidine hydrochloride Step 1: 2-chloro-4-hydroxycyclopenta[d]pyrimidine In accordance with the same procedure as in Step 1 of Example 57, except that 2,4-dichlorocyclopenta[d] pyrimidine (2.7 g, 14.3 mmol) prepared in Step 3 of Example 29 was used as a starting material, 1.7 g of the title compound was prepared. (Yield: 69.7%)

Step 2: 2-(1-Methyl-1,2,3,4-tetrahydroisoquinolin-2-yl)-2-hydroxycyclopenta[d]pyrimidine In accordance with the same procedure as in Step 2 of Example 57, except that 2-chloro-4-hydroxycyclopenta[d] pyrimidine(1.7 g, 10.0 mmol) prepared in the above Step 1 was used as a starting material, 2.2 g of the titled compound was prepared. (Yield: 78.2%)

Step 3: 2-(1-Methyl-1,2,3,4-tetrahydroisoquinolin-2-yl)-4-chlorocyclopenta[d]pyrimidine In accordance with the same procedure as in Step 3 of Example 57, except that 2-(1-methyl-1,2,3,4-tetrahydroisoquinoline-2-yl)-2-hydroxycyclopenta[d]

pyrimidine(2.2 g, 7.8 mmol) prepared in the above Step 2 was used as a starting material, 1.5 g of the titled compound was prepared.
(Yield: 64%)

Step 4: 4-(2-Methyl-4-fluorophenylamino)-2-(1-methyl-1,2,3,4-tetrahydroisoquinolin-2-yl)cyclopenta[d]pyrimidine hydrochloride After 2-methyl-4-fluoroaniline(0.46 ml, 4.2 mmol) was added to a mixture solution of 2-(1-methyl-1,2,3,4-tetrahydroisoquinolin-2-yl)-4-chlorocyclopenta[d]pyrimidine(0.6 g, 2.0 mmol) and dimethylformamide(10 ml), 0.10 g of the titled compound was obtained in accordance with the same procedure as in Step 4 of Example 57.
Yield: 12%
M.P.: 165°–168° C.
$^1$H-NMR(CDCl$_3$): δ 1.40(m, 2H), 1.62(d, 3H), 2.22(m, 2H), 2.30(s, 3H), 2.62–2.98(bd, 3H), 3.30(m, 2H), 3.70(bd, 1H), 4.73(bs, 1H), 5.32(bs, 1H), 6.98(m, 2H), 7.20(m, 5H), 14.02(bd, 1H).

EXAMPLE 82

Synthesis of 2-(2-methyl-4-fluorophenylamino)-4-(1-methyl-1,2,3,4-tetrahydroisoquinolin-2-yl)-5,6,7,8-tetrahydroquinazoline hydrochloride Step 1: 2-chloro-4-hydroxy-5,6,7,8-tetrahydroquinazoline In accordance with the same procedure as in Step 1 of Example 57, except that 2,4-dichloro-5,6,7,8-tetrahydroquinazoline(6.4 g, 31.6 mmol) prepared in the Step 2 of Example 32 was used as a starting material, 4.2 g of the titled compound was prepared. (Yield: 72%)

Step 2: 2-(1-Methyl-1,2,3,4-tetrahydroisoquinolin-2-yl)-4-hydroxy-5,6,7,8-tetrahydroquinazoline In accordance with the same procedure as in Step 2 of Example 57, except that 2-chloro-4-hydroxy-5,6,7,8-tetrahydroquinazoline (2.0 g, 10.8 mmol) prepared in the above Step 1 and 1-methyl-1,2,3,4-tetrahydroisoquinoline (3.3 g, 22.4 mmol) were used as starting materials, 1.1 g of the titled compound was prepared. (Yield: 34.5%)

Step 3: 2-(1-Methyl-1,2,3,4-tetrahydroisoquinolin-2-yl)-4-chloro-5,6,7,8-tetrahydroquinazoline In accordance with the same procedure as in Step 3 of Example 57, except that 2-(1-methyl-1,2,3,4-tetrahydroisoquinoline-2-yl)-4-hydroxy-5,6,7,8-tetrahydroquinazoline (1.1 g, 3.7 mmol) prepared in the above Step 2 was used as a starting material, 0.7 g of the titled compound was prepared.
(Yield: 60.3%)

Step 4: 4-(2-Methyl-4-fluorophenylamino)-2-(1-methyl-1,2,3,4-tetrahydroisoquinolin-2-yl)-5,6,7,8-tetrahydroquinazoline hydrochloride After 4-fluoro-2-methylaniline(0.3 ml, 2.7 mmol) was added to a mixture solution of 2-(1-methyl-1,2,3,4-tetrahydroisoquinolin-2-yl)-4-chloro-5,6,7,8-tetrahydroquinazoline(0.35 g, 1.1 mmol) and dimethylformamide(5 ml), 0.15 g of the titled compound was obtained in accordance with the same procedure as in Step 4 of Example 57.
Yield: 31%
M.P.: 181°–184° C.
$^1$H-NMR(DMSO-d$_6$): δ 1.32(d, 3H), 1.80(bd, 4H), 2.18(s, 3H), 2.85(bd, 4H), 3.40(bd, 1H), 3.65(bd, 2H), 4.25(m, 1H), 5.40(bd, 1H), 7.05–7.38(m, 7H), 9.62(s, 1H), 12.20(s, 1H).

EXAMPLE 83

Synthesis of 4-(2-methyl-4-fluorophenylamino)-2-(1,2,3,4-tetrahydroisoquinolin-2-yl)-5,6,7,8-tetrahydroquinazoline hydrochloride Step 1: 2-(1,2,3,4-tetrahydroisoquinolin-2-yl)-4-hydroxy-5,6,7,8-tetrahydroquinazoline In accordance with the same procedure as in Step 2 of Example 57, except that 2-chloro-4-hydroxy-5,6,7,8-tetrahydroquinazoline (2.0 g, 10.8 mmol) prepared in Step 1 of Example 82 and 1,2,3,4-tetrahydroisoquinoline (2.8 g, 22.4 mmol) were used as starting materials, 0.8 g of the titled compound was prepared. (Yield: 26.3%)

Step 2: 2-(1,2,3,4-tetrahydroisoquinolin-2-yl)-4-chloro-5,6,7,8-tetrahydroquinazoline In accordance with the same procedure as in Step 3 of Example 57, except that 2-(1,2,3,4-tetrahydroisoquinolin-2-yl)-4-hydroxy-5,6,7,8-tetrahydroquinazoline(0.8 g, 2.8 mmol) prepared in the above Step 1 was used as a starting material, 0.6 g of the titled compound was prepared. (Yield: 71.5%)

Step 3: 4-(2-Methyl-4-fluorophenylamino)-2-(1,2,3,4-tetrahydroisoquinolin-2-yl)-5,6,7,8-tetrahydroquinazoline hydrochloride After 4-fluoro-2-methylaniline(0.3 ml, 2.7 mmol) was added to a mixture solution of 2-(1,2,3,4-tetrahydroisoquinolin-2-yl)-4-chloro-5,6,7,8-tetrahydroquinazoline(0.3 g, 1.0 mmol) and dimethylformamide(5 ml), 0.2 g of the titled compound was prepared in accordance with the same procedure as in Step 4 of Example 57.
Yield: 47.1%
M.P.: 150°–152° C.
$^1$H-NMR(DMSO-d$_6$): δ 1.76(bd, 4H), 2.15(s, 3H), 2.81(bd, 4H), 3.46(bd, 2H), 3.77(bd, 2H), 4.74(s, 1H), 7.02–7.33(m, 7H), 9.59(s, 1H), 12.40(bd, 1H).

Test 1: Inhibition of proton pump($H^+/K^+$ ATPase) activity

A proton pump enzyme source was prepared by the same method as in Experiment 1-1 of WO 94/14795. Further, the inhibitory effect of proton pump activity was measured by the same method as in Experiment 1-2 of WO 94/14795.

Namely, the proton pump activity stimulated by $Mg^{++}$ was used as a negative comparative group, and the activity stimulated by $Mg^{++}$ and $K^+$ was used as a positive comparative group. The comparative compound was omeprazole.

Test tubes were divided into 4 groups: Group 1 as negative comparative group(n=3), Group 2 as positive comparative group(n=3), Group 3(n=5×2) to be administered with the compound of the present invention and Group 4(n=5×2) to be administered with the comparative compound.

The inhibitory effects of Groups 3 and 4 on proton pump activity were measured by employing the compound prepared in Example and omeperazole, respectively, each of which was dissolved in dimethylsulfoxide at 5 different concentrations.

To each of Groups 1, 2, 3 and 4 were added 100 μl of magnesium chloride(40 mM) dissolved in 40 mM Tris-HCl buffer(pH 6.0) and 100μ of the enzyme source. Then, 50μ of potassium chloride(50 mM) and 50 μl of ammonium chloride(6 mM) dissolved in 40 mM Tris-HCl buffer(pH 6.0) were added to all groups except for Group 1.

10 μl of dimethylsulfoxide was added to each of Groups 1 and 2; and to Group 3 was added 10 μl of the solution in which the compound prepared in Example was dissolved in dimethylsulfoxide at 5 different concentrations(n=5×2). To Group 4, 10 μl of the solution prepared by dissolving omeprazole in dimethylsulfoxide at 5 different concentrations(37.6, 21.4, 12.2, 7.0 and 4.0 μM) was added (n=5×2). 40 mM Tris-HCl buffer(pH=6.0) was added thereto so as to make the total volume 400 μl.

Thereafter, the test tubes of each Group were placed at 37° C. for 30 minutes for the preincubation. 100 μl of ATP solution (6.6 mM) was added until the reaction volume became 500 μl. After the reaction was carried out at 37° C. for 30 minutes, 25% cold trichloroacetic acid was added to terminate the enzyme reaction. The released inorganic phosphate was measured by an automatic analyzer(Express 550, Corning).

The difference between Group 1 and Group 2 represents the proton pump activity activated by K⁺ only. The inhibition percentages of Groups 3 and 4 were calculated from Litchfield-wilcoxon equation[see, e.g., *J. pharmacol. Exp. Ther.*, 96, 99(1949)]. The concentrations of the test compounds which inhibit 50% of the proton pump activity are represented as IC50 in Table 1.

TABLE 1

| Test compound | IC50 (μM) | | Effect ratio |
|---|---|---|---|
| | Test compound | Omeprazole | |
| Example 1 | 5.4 | 5.8 | 1.08 |
| Example 2 | 0.9 | 7.3 | 7.82 |
| Example 3 | 3.5 | 7.3 | 2.11 |
| Example 5 | 1.3 | 6.4 | 4.91 |
| Example 6 | 4.3 | 6.4 | 4.91 |
| Example 8 | ~12.5 | 7.7 | ~0.60 |
| Example 9 | ~10.0 | 11.2 | ~1.12 |
| Example 10 | 10.6 | 7.3 | 0.69 |
| Example 12 | 0.6 | 5.8 | 9.83 |
| Example 13 | 0.5 | 5.8 | 10.70 |
| Example 14 | 0.7 | 5.8 | 8.70 |
| Example 15 | 1.6 | 5.8 | 3.69 |
| Example 16 | 1.5 | 5.8 | 3.80 |
| Example 17 | 1.8 | 5.8 | 3.20 |
| Example 18 | 4.2 | 11.4 | 2.69 |
| Example 19 | 3.9 | 11.4 | 2.92 |
| Example 20 | 4.4 | 11.4 | 2.59 |
| Example 21 | 1.5 | 10.9 | 7.33 |
| Example 22 | 1.4 | 10.9 | 7.26 |
| Example 23 | 2.0 | 10.9 | 5.45 |
| Example 24 | 0.6 | 10.9 | 19.33 |
| Example 25 | 1.4 | 11.1 | 8.10 |
| Example 26 | 0.8 | 12.6 | 15.62 |
| Example 27 | 2.1 | 12.9 | 6.26 |
| Example 28 | >15.0 | 14.2 | <0.95 |
| Example 29 | 0.4 | 6.4 | 17.49 |
| Example 30 | ~8.4 | 14.2 | ~1.69 |
| Example 31 | ~15.0 | 7.1 | ~0.51 |
| Example 32 | 1.2 | 10.1 | 8.40 |
| Example 34 | 1.0 | 10.1 | 4.02 |
| Example 35 | 2.5 | 10.1 | 4.02 |
| Example 37 | 0.7 | 7.1 | 9.85 |
| Example 38 | 2.2 | 7.1 | 3.24 |
| Example 39 | >15.0 | 14.2 | <0.95 |
| Example 40 | 0.7 | 6.4 | 9.17 |
| Example 41 | 0.6 | 10.1 | 18.10 |
| Example 42 | 1.5 | 7.3 | 4.95 |
| Example 43 | 0.5 | 7.1 | 14.44 |
| Example 44 | ~11.3 | 12.2 | ~1.08 |
| Example 45 | 3.1 | 12.90 | 4.12 |
| Example 46 | ~19.2 | 12.20 | ~0.60 |
| Example 47 | ~5.0 | 7.70 | ~1.54 |
| Example 48 | ~5.5 | 10.80 | ~1.97 |
| Example 49 | ~10.8 | 12.20 | ~1.13 |
| Example 50 | ~16.9 | 12.20 | ~0.70 |
| Example 51 | 1.1 | 8.00 | 7.05 |
| Example 52 | 0.5 | 11.40 | 21.11 |
| Example 53 | 2.1 | 11.40 | 5.38 |
| Example 54 | 20.6 | 10.10 | 0.49 |
| Example 55 | 2.1 | 10.10 | 4.80 |
| Example 57 | 3.3 | 11.5 | 3.50 |
| Example 58 | >25.0 | 11.3 | <0.45 |
| Example 59 | ~12.5 | 7.7 | ~0.60 |
| Example 60 | ~15.0 | 7.7 | ~0.51 |
| Example 61 | ~12.5 | 7.7 | ~0.60 |
| Example 62 | >20.0 | 14.2 | <0.71 |
| Example 63 | ~12.0 | 14.2 | ~1.18 |
| Example 64 | ~10.0 | 14.2 | ~1.42 |

TABLE 1-continued

| Test compound | IC50 (μM) | | Effect ratio |
|---|---|---|---|
| | Test compound | Omeprazole | |
| Example 65 | 1.0 | 5.8 | 6.04 |
| Example 66 | 0.9 | 5.8 | 6.40 |
| Example 67 | 1.3 | 5.8 | 4.50 |
| Example 68 | 3.1 | 5.8 | 1.86 |
| Example 69 | 2.9 | 5.8 | 2.00 |
| Example 70 | 3.5 | 5.8 | 1.70 |
| Example 74 | 0.5 | 10.1 | 22.00 |
| Example 75 | 1.2 | 7.1 | 5.89 |
| Example 77 | 3.6 | 11.4 | 3.16 |
| Example 78 | 8.5 | 11.4 | 1.35 |
| Example 81 | 0.4 | 6.4 | 15.82 |
| Example 82 | 1.1 | 10.1 | 9.40 |
| Example 83 | 1.4 | 7.3 | 5.34 |

Test 2: Inhibition of gastric secretion

In accordance with the method disclosed in journal [Shay, H., et al., *Gastroenterology*, 5, 43–61(1945), inhibitory effect on gastric secretion was carried out.

Male Sprague-Dawley rats having a body weight of 200±10 g were divided into 3 groups(n=5) and fasted for 24 hours before the experiment with free access to water. Under ether anesthesia, the abdomen was incised, and the pylorus was ligated. As a comparative group, Group 1 was administered intraduodenally in a volume of 0.5 mg/200 g of 30% aqueous polyethylene glycol 400 solution. Groups 2 and 3 were administered intraduodenally with the compound of Example and omeprazole, respectively, each of which was suspended in 30% aqueous polyethylene glycol 400 solution at a concentration of 20 mg/kg. After closing the abdominal cavity, the rats were placed for 5 hours and then killed by cervical dislocation. The stomach was extracted to obtain gastric juice.

The gastric juice was centrifuged at 1,000 g to remove precipitates. The amount and acidity of the gastric juice were measured. Relative volumes, relative acid concentrations and relative acid outputs of the test compounds were calculated from equations(I), (II) and (III) and the results are shown in Table 2.

Relative volume=(the average amount of gastric juice of Group 1−the average amount of gastric juice of Group 2)/(the average amount of gastric juice of group 1−the average amount of gastric juice of Group 3)    (I)

Relative acid concentration=(the average acidity of Group 1−the average acidity of Group 2)/(the average acidity of Group 1−the average acidity of Group 3)    (II)

Relative acid output=(the total amount of acid output of Group 1−the total amount of acid output of Group 2)/(the total amount of acid output of Group 1−the total amount of acid output of Group 3).    (III)

TABLE 2

| Compound | Rel. Vol. (%) | Rel. Conc. (%) | Relative Acid Output |
|---|---|---|---|
| Example 1 | 0.12 | 0.00 | 0.11 |
| Example 2 | 0.92 | 0.8 | 0.89 |
| Example 3 | 0.76 | 0.81 | 0.87 |
| Example 4 | 0.99 | 0.56 | 0.87 |
| Example 5 | 0.59 | 0.27 | 0.61 |
| Example 6 | 0.64 | 0.28 | 0.64 |
| Example 7 | 0.51 | 0.09 | 0.48 |
| Example 8 | 0.43 | 0.12 | 0.42 |
| Example 9 | 0.4 | −0.03 | 0.3 |

TABLE 2-continued

| Compound | Rel. Vol. (%) | Rel. Conc. (%) | Relative Acid Output |
|---|---|---|---|
| Example 10 | 0.58 | 0.47 | 0.55 |
| Example 11 | 0.99 | 0.41 | 0.82 |
| Example 12 | 1.64 | 0.29 | 0.75 |
| Example 13 | 1.72 | 0.46 | 0.81 |
| Example 14 | 0.53 | 0.3 | 0.72 |
| Example 15 | 0.8 | 1.06 | 0.99 |
| Example 16 | 0.96 | 1.24 | 1.13 |
| Example 17 | 0.82 | 0.97 | 0.89 |
| Example 18 | 1.72 | 1.82 | 1.39 |
| Example 19 | 1.8 | 1.86 | 1.43 |
| Example 20 | 1.66 | 1.75 | 1.28 |
| Example 21 | 1.06 | 0.88 | 0.97 |
| Example 22 | 0.99 | 0.80 | 0.90 |
| Example 23 | 0.92 | 0.78 | 0.88 |
| Example 24 | 1.00 | 1.03 | 1.01 |
| Example 25 | 1.06 | 0.80 | 0.92 |
| Example 26 | 0.6 | 0.53 | 0.73 |
| Example 27 | 0.7 | 0.61 | 0.81 |
| Example 28 | 0.71 | 0.44 | 0.78 |
| Example 29 | 0.56 | 0.31 | 0.6 |
| Example 30 | 0.33 | 0.2 | 0.39 |
| Example 31 | 0.83 | 0.21 | 0.74 |
| Example 32 | 1.03 | 0.97 | 0.91 |
| Example 33 | 0.93 | 1.13 | 0.94 |
| Example 34 | 0.99 | 1 | 0.99 |
| Example 35 | 1.05 | 0.84 | 0.94 |
| Example 36 | 0.65 | 0.05 | 0.41 |
| Example 37 | 0.82 | 0.42 | 0.82 |
| Example 38 | 0.74 | 0.37 | 0.74 |
| Example 39 | 0.58 | 0.18 | 0.56 |
| Example 40 | 0.71 | 0.36 | 0.74 |
| Example 41 | 0.94 | 1.87 | 1.12 |
| Example 42 | 1.15 | 1.4 | 1.15 |
| Example 43 | 0.7 | 0.59 | 0.82 |
| Example 44 | 0.27 | 0.33 | 0.41 |
| Example 45 | 0.84 | 0.75 | 0.89 |
| Example 46 | 0.73 | 0.44 | 0.74 |
| Example 47 | 0.38 | 0.14 | 0.38 |
| Example 48 | 0.17 | 0.04 | 0.16 |
| Example 49 | 0.2 | 0.02 | 0.16 |
| Example 50 | 0.72 | 0.29 | 0.66 |
| Example 51 | 0.59 | 0.12 | 0.59 |
| Example 52 | 1.34 | 0.94 | 1.12 |
| Example 53 | 0.47 | 1.14 | 0.55 |
| Example 54 | 0.86 | 0.23 | 0.75 |
| Example 55 | 0.56 | 0.11 | 0.51 |
| Example 56 | 0.01 | 0.08 | 0.08 |
| Example 57 | 1.20 | 0.27 | 0.61 |
| Example 58 | 0.58 | 0.16 | 0.35 |
| Example 59 | 0.51 | 0.25 | 0.56 |
| Example 60 | 0.65 | 0.28 | 0.65 |
| Example 61 | 0.32 | 0.22 | 0.40 |
| Example 62 | 0.61 | 0.31 | 0.67 |
| Example 63 | 0.69 | 0.33 | 0.72 |
| Example 64 | 0.34 | 0.26 | 0.40 |
| Example 65 | 1.43 | 0.35 | 0.71 |
| Example 66 | 1.49 | 0.47 | 0.85 |
| Example 67 | 1.36 | 0.31 | 0.62 |
| Example 68 | 1.52 | 0.23 | 0.67 |
| Example 69 | 1.61 | 0.39 | 0.76 |
| Example 70 | 1.30 | 0.22 | 0.61 |
| Example 71 | 0.25 | −0.07 | 0.16 |
| Example 72 | 0.34 | 0.16 | 0.25 |
| Example 73 | 0.18 | −0.05 | 0.13 |
| Example 74 | 1.22 | 1.49 | 1.16 |
| Example 75 | 1.30 | 1.62 | 1.20 |
| Example 76 | 0.28 | 0.17 | 0.33 |
| Example 77 | 1.48 | 1.63 | 1.30 |
| Example 78 | 1.06 | 1.75 | 1.09 |
| Example 79 | 0.54 | 1.28 | 0.49 |
| Example 80 | 0.32 | 0.29 | 0.44 |
| Example 81 | 0.56 | 0.47 | 0.68 |
| Example 82 | 0.69 | 0.59 | 0.79 |
| Example 83 | 1.19 | 1.29 | 1.13 |

Test 3. Reversibility Test

Gastric vesicles were prepared by the same method as in Experiment 4-1 of WO 94/14795. The inhibition mechanism of proton pump activity by the present invention compound was tested in accordance with the so-called Dilution and Washout method [see e.g., D. J. Keeling, et al., *Biochemical Pharmacology*, 42(1), 123–130(1991)].

Namely, test tubes were divided into two group, Groups 1 and 2. Each group was divided into four subgroups. 90 μl of 5 mM Pipes/Tris buffer(pH 7.4) and 10 μl of DMSO were added to subgroups 1 and 2 of each group. 90 μl of 5 mM Pipes/Tris buffer(pH 7.4) and 10 μl of the compound prepared in Example 43(50 μM) were added to subgroups 3 and 4 of each group. To all two groups, was added 100 μl of lyophilized vesicles at the concentration of 100 μg protein/ml and then preincubated at 37° C. for 15 minutes.

2 mM $MgCl_2$ was added to subgroups 1 and 3 of Group 1. 2 mM $MgCl_2$ and 10 mM KCl were added to subgroups 2 and 4 of Group 1. 3 mM ATP was added to all subgroups of Group 1 until the final volume became 500 μl. After incubation for 30 minutes, the inhibition of $H^+/K^+$-ATPase activity by the test compound was measured.

After preincubation as described above, each subgroup of Group 2 was diluted with 50-fold volume of 5 mM Pipes/Tris buffer(pH7.4) and then centrifuged for 60 minutes by means of Beckman ultracentrifuge(Model L8-80). The supernatant was discarded and washed out by 10 ml of 5 mM Pipes/Tris buffer(ph 7.4). The resulting pellet was suspended with 5 mM Pipes/Tris buffer (pH7.4) until the volume became the same as the preincubation volume.

Thereafter, in accordance with the treatment to Group 1, each subgroup of Group 2 was treated with 2 mM $MgCl_2$, 10 mM KCl and 3 mM ATP. And the final volume of each subgroup of Group 2 was made to be 500 μl. After incubation at 37° C. for 30 minutes, the inhibition of $H^+/K^+$-ATPase activity was measured.

And it was further measured in accordance with the same procedures as above, except the compound prepared in Example 75 was used as a test compound. The inhibition of $H^+/K^+$ ATPase activity before and after the Dilution and Washout procedures is shown in Table 3.

TABLE 3

| Compound | Dilution & Washout | |
|---|---|---|
|  | Before | After |
| Example 43 | 62 | 6 |
| Example 75 | 66.6 | 15 |

As shown in Table 3, the compounds of Examples 43 and 75 inhibit the enzyme activity by 62% and 66.6% before the Dilution and Washout procedure, whereas they show 6 or 15% of inhibition of the enzyme activity after the Dilution and Washout procedure. This indicates that the inhibition of the enzyme activity of the present invention compounds is reversible.

While the invention has been described with respect to the specific embodiments, it should be recognized that various modifications and changes may be made by those skilled in the art to the invention which also fall within the scope of the invention as defined as the appended claims.

What is claimed is:

1. Pyrimidine derivative compounds of formulae (I-1) and (I-2) inclusive of pharmaceutically acceptable salts thereof:

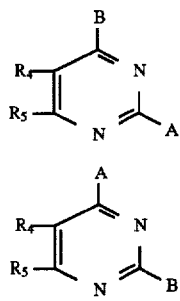

(I-1)

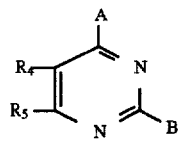

(I-2)

wherein:

R$_4$ and R$_5$, which may be the same or different, are independently hydrogen or a C$_1$-C$_3$ alkyl group, or jointly form a cyclopentyl or cyclohexyl ring;

A is a group of formula(II):

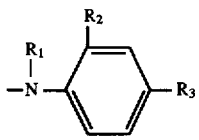

(II)

wherein R$_1$ and R$_2$ are, independently of each other, hydrogen or a C$_1$-C$_3$ alkyl group, and R$_3$ is hydrogen, a C$_1$-C$_3$ alkyl group or a halogen; and B is 1-(substituted)-1,2,3,4-tetrahydroisoquinolin-2-yl of formula (III-1) or 7-(substituted)-4,5,6,7-tetrahydrothieno[2,3-c]pyridin-6-yl of formula (III-2)

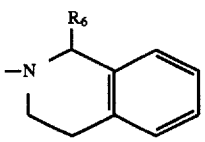

(III-1)

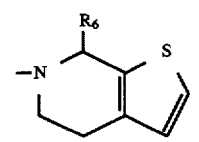

(III-2)

wherein R$_6$ is hydrogen or a C$_1$-C$_3$ alkyl group.

2. The compound of claim 1, which is selected from the group consisting of:

2-(2-methyl-4-fluorophenylamino)-4-(1-methyl-1,2,3,4-tetrahydroisoquinolin-2-yl)pyrimidine hydrochloride;
6-methyl-2-(2-methyl-4-fluorophenylamino)-4-(1-methyl-1,2,3,4-tetrahydroisoquinolin-2-yl)pyrimidine hydrochloride;
6-methyl-4-(1-methyl-1,2,3,4-tetrahydroisoquinolin-2-yl)-2-(4-fluorophenylamino)pyrimidine hydrochloride;
6-methyl-2-(N-methylphenylamino)-4-(1-methyl-1,2,3,4-tetrahydroisoquinolin-2-yl)pyrimidine hydrochloride;
6-ethyl-2-(2-methyl-4-fluorophenylamino)-4-(1-methyl-1,2,3,4-tetrahydroisoquinolin-2-yl)pyrimidine hydrochloride;
6-ethyl-2-(4-fluorophenylamino)-4-(1-methyl-1,2,3,4-tetrahydroisoquinolin-2-yl)pyrimidine hydrochloride;
6-ethyl-2-(N-methylphenylamino)-4-(1-methyl-1,2,3,4-tetrahydroisoquinolin-2-yl)pyrimidine hydrochloride;
6-ethyl-2-(2-methylphenylamino)-4-(1-methyl-1,2,3,4-tetrahydroisoquinolin-2-yl)pyrimidine hydrochloride;
2-(2-methyl-4-fluorophenylamino)-4-(1-methyl-1,2,3,4-tetrahydroisoquinolin-2-yl)-6-propylpyrimidine hydrochloride;
4-(1-methyl-1,2,3,4-tetrahydroisoquinolin-2-yl)-6-propyl-2-(4-fluorophenylamino)pyrimidine hydrochloride;
2-(N-methylphenylamino)-4-(1-methyl-1,2,3,4-tetrahydroisoquinolin-2-yl)-6-propylpyrimidine hydrochloride;
5,6-dimethyl-2-(2-methyl-4-fluorophenylamino)-4-(1-methyl-1,2,3,4-tetrahydroisoquinolin-2-yl)pyrimidine hydrochloride;
(R)-5,6-dimethyl-2-(2-methyl-4-fluorophenylamino)-4-(1-methyl-1,2,3,4-tetrahydroisoquinolin-2-yl)pyrimidine hydrochloride;
(S)-5,6-dimethyl-2-(2-methyl-4-fluorophenylamino)-4-(1-methyl-1,2,3,4-tetrahydroisoquinolin-2-yl)pyrimidine hydrochloride;
5,6-dimethyl-2-(4-fluorophenylamino)-4-(1-methyl-1,2,3,4-tetrahydroisoquinolin-2-yl)pyrimidine hydrochloride;
(R)-5,6-dimethyl-2-(4-fluorophenylamino)-4-(1-methyl-1,2,3,4-tetrahydroisoquinolin-2-yl)pyrimidine hydrochloride;
(S)-5,6-dimethyl-2-(4-fluorophenylamino)-4-(1-methyl-1,2,3,4-tetrahydroisoquinolin-2-yl)pyrimidine hydrochloride;
5,6-dimethyl-2-(N-methylphenylamino)-4-(1-methyl-1,2,3,4-tetrahydroisoquinolin-2-yl)pyrimidine hydrochloride;
(R)-5,6-dimethyl-2-(N-methylphenylamino)-4-(1-methyl-1,2,3,4-tetrahydroisoquinolin-2-yl)pyrimidine hydrochloride;
(S)-5,6-dimethyl-2-(N-methylphenylamino)-4-(1-methyl-1,2,3,4-tetrahydroisoquinolin-2-yl)pyrimidine hydrochloride;
5,6-dimethyl-2-(phenylamino)-4-(1-methyl-1,2,3,4-tetrahydroisoquinolin-2-yl)pyrimidine hydrochloride;
(R)-5,6-dimethyl-2-(4-phenylamino)-4-(1-methyl-1,2,3,4-tetrahydroisoquinolin-2-yl)pyrimidine hydrochloride;
(S)-5,6-dimethyl-2-(4-fluorophenylamino)-4-(1-methyl-1,2,3,4-tetrahydroisoquinolin-2-yl)pyrimidine hydrochloride;
5,6-dimethyl-2-(2-methylphenylamino)-4-(1-methyl-1,2,3,4-tetrahydroisoquinolin-2-yl)pyrimidine hydrochloride;
5,6-dimethyl-2-(4-methylphenylamino)-4-(1-methyl-1,2,3,4-tetrahydroisoquinolin-2-yl)pyrimidine hydrochloride;
5-methyl-6-ethyl-2-(2-methyl-4-fluorophenylamino)-4-(1-methyl-1,2,3,4-tetrahydroisoquinolin-2-yl)pyrimidine hydrochloride;
5-methyl-6-ethyl-2-(4-fluorophenylamino)-4-(1-methyl-1,2,3,4-tetrahydroisoquinolin-2-yl)pyrimidine hydrochloride;
5-methyl-6-ethyl-2-(N-methylphenylamino)-4-(1-methyl-1,2,3,4-tetrahydroisoquinolin-2-yl)pyrimidine hydrochloride;
2-(2-methyl-4-fluorophenylamino)-4-(1-methyl-1,2,3,4-tetrahydroisoquinolin-2-yl)cyclopenta[d]pyrimidine hydrochloride;
2-(4-fluorophenylamino)-4-(1-methyl-1,2,3,4-tetrahydroisoquinolin-2-yl)cyclopenta[d]pyrimidine hydrochloride;
2-(N-methylphenylamino)-4-(1-methyl-1,2,3,4-tetrahydroisoquinolin-2-yl)cyclopenta[d]pyrimidine hydrochloride;
2-(2-methyl-4-fluorophenylamino)-4-(1-methyl-1,2,3,4-tetrahydroisoquinolin-2-yl)-5,6,7,8-tetrahydroquinazoline hydrochloride;
2-(N-methylphenylamino)-4-(1-methyl-1,2,3,4-tetrahydroisoquinoline-2-yl)-5,6,7,8-tetrahydroquinazoline hydrochloride;
6-methyl-2-(2-methyl-4-fluorophenylamino)-4-(1,2,3,4-tetrahydroisoquinolin-2-yl)pyrimidine hydrochloride;
6-methyl-2-(4-fluorophenylamino)-4-(1,2,3,4-tetrahydroisoquinoline-2-yl )pyrimidine hydrochloride;
6-methyl-2-(N-methylphenylamino)-4-(1,2,3,4-tetrahydroisoquinolin-2-yl)pyrimidine hydrochloride;
6-ethyl-2-(2-methyl-4-fluorophenylamino)-4-(1,2,3,4-tetrahydroisoquinolin-2-yl)pyrimidine hydrochloride;
6-ethyl-2-(4-fluorophenylamino)-4-(1,2,3,4-tetrahydroisoquinolin-2-yl)pyrimidine hydrochloride;
6-ethyl-2-(N-methylphenylamino)-4-(1,2,3,4-tetrahydroisoquinolin-2-yl)pyrimidine hydrochloride;

6-ethyl-2-(2-methylphenylamino)-4-(1,2,3,4-tetrahydroisoquinolin-2-yl)pyrimidine hydrochloride;
5,6-dimethyl-2-(2-methyl-4-fluorophenylamino)-4-(1,2,3,4-tetrahydroisoquinolin-2-yl)pyrimidine hydrochloride;
5,6-dimethyl-2-(4-fluorophenylamino)-4-(1,2,3,4-tetrahydroisoquinolin-2-yl)pyrimidine hydrochloride;
5,6-dimethyl-2-(N-methylphenylamino)-4-(1,2,3,4-tetrahydroisoquinolin-2-yl)pyrimidine hydrochloride;
5-methyl-6-ethyl-2-(2-methyl-4-fluorophenylamino)-4-(1,2,3,4-tetrahydroisoquinolin-2-yl)pyrimidine hydrochloride;
5-methyl-6-ethyl-2-(4-fluorophenylamino)-4-(1,2,3,4-tetrahydroisoquinolin-2-yl)pyrimidine hydrochloride;
5-methyl-6-ethyl-2-(N-methylphenylamino)-4-(1,2,3,4-tetrahydroisoquinolin-2-yl)pyrimidine hydrochloride;
2-(2-methyl-4-fluorophenylamino)-4-(1,2,3,4-tetrahydroisoquinolin-2-yl)cyclopenta[d]pyrimidine hydrochloride;
2-(2-methyl-4-fluorophenylamino)-4-(1,2,3,4-tetrahydroisoquinolin-2-yl)-5,6,7,8-tetrahydroquinazolinehydrochloride;
2-(4-fluorophenylamino)-4-(1,2,3,4-tetrahydroisoquinolin-2-yl)-5,6,7,8-tetrahydroquinazoline hydrochloride;
2-(N-methylphenylamino)-4-(1,2,3,4-tetrahydroisoquinolin-2-yl)-5,6,7,8-tetrahydroquinazoline hydrochloride;
2-(2-methylphenylamino)-4-(1,2,3,4-tetrahydroisoquinolin-2-yl)-5,6,7,8-tetrahydroquinazoline hydrochloride;
6-methyl-2-(2-methyl-4-fluorophenylamino)-4-(7-methyl-4,5,6,7-tetrahydrothieno[2,3-c]pyridin-6-yl)pyrimidine hydrochloride;
6-methyl-4-(7-methyl-4,5,6,7-tetrahydrothieno[2,3-c]pyridin-6-yl)-2-(4-fluorophenylamino)pyrimidine hydrochloride;
6-methyl-2-(N-methylphenylamino)-4-(7-methyl-4,5,6,7-tetrahydrothieno[2,3-c]pyridin-6-yl)pyrimidine hydrochloride;
5,6-dimethyl-2-(2-methyl-4-fluorophenylamino)-4-(7-methyl-4,5,6,7-tetrahydrothieno[2,3-c]pyridin-6-yl)pyrimidine hydrochloride;
5-methyl-2-(2-methyl-4-fluorophenylamino)-4-(7-methyl-4,5,6,7-tetrahydrothieno[2,3-c]pyridin-6-yl)-6-ethylpyrimidine hydrochloride;
6-methyl-4-(2-methyl-4-fluorophenylamino)-2-(1-methyl-1,2,3,4-tetrahydroisoquinolin-2-yl)pyrimidine hydrochloride;
6-methyl-4-(4-fluorophenylamino)-2-(1-methyl-1,2,3,4-tetrahydroisoquinolin-2-yl)pyrimidine hydrochloride;
6-methyl-4-(2-methyl-4-fluorophenylamino)-2-(7-methyl-4,5,6,7-tetrahydrothieno[2,3-c]pyridin-6-yl)pyrimidine hydrochloride;
6-methyl-4-(4-fluorophenylamino)-2-(7-methyl-4,5,6,7-tetrahydrothieno[2,3-c]pyridin-6-yl)pyrimidine hydrochloride;
6-ethyl-2-(2-methyl-4-fluorophenylamino)-4-(1-methyl-1,2,3,4-tetrahydroisoquinolin-2-yl)pyrimidine hydrochloride;
6-ethyl-4-(2-methyl-4-fluorophenylamino)-2-(1,2,3,4-tetrahydroisoquinolin-2-yl)pyrimidine hydrochloride;
6-ethyl-4-(4-fluorophenylamino)-2-(1,2,3,4-tetrahydroisoquinolin-2-yl)pyrimidine hydrochloride;
6-ethyl-4-(N-methylphenylamino)-2-(1,2,3,4-tetrahydroisoquinolin-2-yl)pyrimidine hydrochloride;
5,6-dimethyl-4-(2-methyl-4-fluorophenylamino)-2-(1-methyl-1,2,3,4-tetrahydroisoquinolin-2-yl)pyrimidine hydrochloride;
(R)-5,6-dimethyl-4-(2-methyl-4-fluorophenylamino)-2-(1-methyl-1,2,3,4-tetrahydroisoquinolin-2-yl)pyrimidine hydrochloride;
(S)-5,6-dimethyl-4-(2-methyl-4-fluorophenylamino)-2-(1-methyl-1,2,3,4-tetrahydroisoquinolin-2-yl)pyrimidine hydrochloride;
5,6-dimethyl-4-(4-fluorophenylamino)-2-(1-methyl-1,2,3,4-tetrahydroisoquinolin-2-yl )pyrimidine hydrochloride;
(R)-5,6-dimethyl-4-(4-fluorophenylamino)-2-(1-methyl-1,2,3,4-tetrahydroisoquinolin-2-yl)pyrimidine hydrochloride;
(S)-5,6-dimethyl-4-(4-fluorophenylamino)-2-(1-methyl-1,2,3,4-tetrahydroisoquinolin-2-yl)pyrimidine hydrochloride;
5,6-dimethyl-4-(N-methylphenylamino)-2-(1-methyl-1,2,3,4-tetrahydroisoquinolin-2-yl)pyrimidine hydrochloride;
(R)-5,6-dimethyl-4-(N-methylphenylamino)-2-(1-methyl-1,2,3,4-tetrahydroisoquinolin-2-yl)pyrimidine hydrochloride;
(S)-5,6-dimethyl-4-(N-methylphenylamino)-2-(1-methyl-1,2,3,4-tetrahydroisoquinolin-2-yl)pyrimidine hydrochloride;
5,6-dimethyl-4-(2-methyl-4-fluorophenylamino)-2-(1,2,3,4-tetrahydroisoquinolin-2-yl)pyrimidine hydrochloride;
5,6-dimethyl-4-(4-fluorophenylamino)-2-(1,2,3,4-tetrahydroisoquinolin-2-yl)pyrimidine hydrochloride;
5,6-dimethyl-4-(N-methylphenylamino)-2-(1,2,3,4-tetrahydroisoquinolin-2-yl)pyrimidine hydrochloride;
5,6-dimethyl-4-(2-methyl-4-fluorophenylamino)-2-(7-methyl-4,5,6,7-tetrahydrothieno[2,3-c]pyridin-6-yl)pyrimidine hydrochloride;
5,6-dimethyl-2-(7-methyl-4,5,6,7-tetrahydrothieno[2,3-c]pyridin-6-yl)-4-(4-fluorophenylamino)pyrimidine hydrochloride;
5,6-dimethyl-4-(N-methylphenylamino)-2-(7-methyl-4,5,6,7-tetrahydrothieno[2,3-c]pyridin-6-yl)pyrimidine hydrochloride;
5-methyl-6-ethyl-4-(2-methyl-4-fluorophenylamino)-2-(1-methyl-1,2,3,4-tetrahydroisoquinolin-2-yl)pyrimidine hydrochloride;
4-(2-methyl-4-fluorophenylamino)-2-(1-methyl-1,2,3,4-tetrahydroisoquinolin-2-yl)cyclopenta[d]pyrimidine hydrochloride;
2-(2-methyl-4-fluorophenylamino)-4-(1-methyl-1,2,3,4-tetrahydroisoquinolin-2-yl)-5,6,7,8-tetrahydroquinazoline hydrochloride; and
4-(2-methyl-4-fluorophenylamino)-2-(1,2,3,4-tetrahydroisoquinolin-2-yl)-5,6,7,8-tetrahydroquinazoline hydrochloride.

3. The compound of claim 1, wherein the pharmaceutically acceptable salts are hydrochlorides, sulfates, phosphates, nitrates, tartrates, fumarates, citrates, mesylates or acetates of the pyrimidine derivative compounds of formulae (I-1) and (I-2).

4. A process for preparing a pyrimidine derivative compound of formula (I-1), which comprises reacting a compound of formula(IV) with a compound of formula (V-1) or (V-2) to give a compound of formula(VI-1); and reacting the compound of formula(VI-1) with a compound of formula (VII):

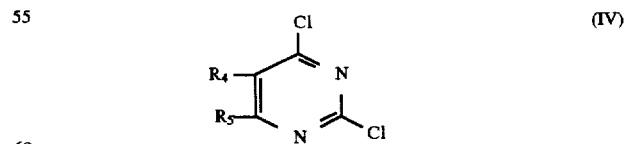

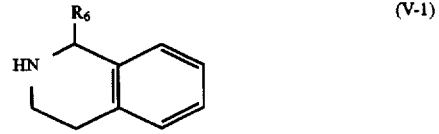

-continued

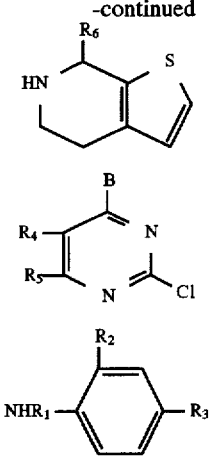

wherein B, $R_1$, $R_2$, $R_3$, $R_4$, $R_5$ and $R_6$ are the same as defined in claim 1.

5. The process of claim 4, wherein the reaction of the compound of formula (IV) with the compound of formula (V-1) or (V-2) is carried out in the presence of a solvent selected from the group consisting of dichloromethane, acetone, acetonitrile and dimethylformamide, and a base selected from the group consisting of triethylamine, N,N-dimethylaniline and pyridine.

6. A process for preparing a pyrimidine derivative compound of formula (I-2), which comprises: hydrolyzing a compound of formula(IV) at its 4-position to give a compound of formula(VIII); reacting the compound of formula (VIII) with a compound of formula (V-1) or (V-2) to give a compound of formula(IX); chlorinating the compound of formula(IX) at its 4-position to give a compound of formula (VI-2); and then reacting the compound of formula (VI-2) with a compound of formula (VII):

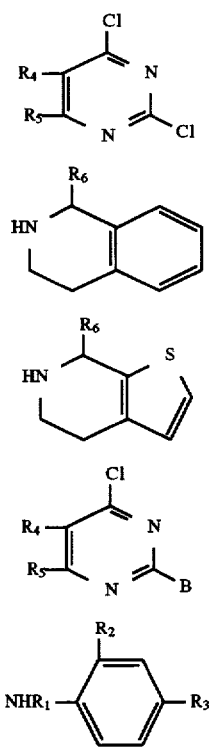

-continued

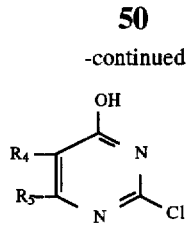

wherein B, $R_1$, $R_2$, $R_3$, $R_4$, $R_5$ and $R_6$ are the same as defined in claim 1.

7. The process of claim 6, where the reaction of the compound of formula (VIII) with the compound of formula (V-1) or (V-2) is carried out in the presence of a solvent selected from the group consisting of dichloromethane, acetone, acetonitrile and dimethylformamide, and a base selected from the group consisting of triethylamine, N,N-dimethylaniline and pyridine.

8. Pyrimidine derivative compounds of formulae (VI-1) and (VI-2):

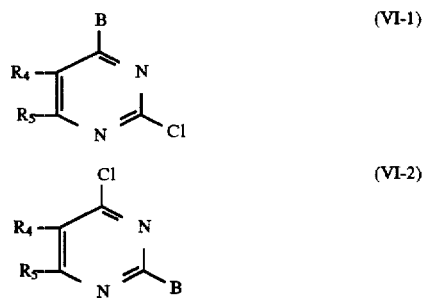

wherein B, $R_4$ and $R_5$ are the same as defined in claim 1.

9. A process for preparing a compound of formula (VI-1), which comprises reacting a compound of formula(IV) with a compound of formula (V-1) or (V-2):

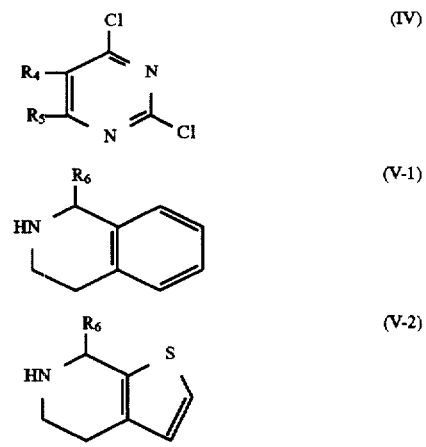

wherein $R_4$, $R_5$ and $R_6$ are the same as defined in claim 1.

10. The process of claim 9, wherein the reaction of the compound of formula (IV) with the compound of formula (V-1) or (V-2) is carried out in the presence of a solvent selected from the group consisting of dichloromethane, acetone, acetonitrile and dimethylformamide, and a base selected from the group consisting of triethylamine, N,N-dimethylaniline and pyridine.

11. A process for preparing a compound of formula (VI-2), which comprises: hydrolyzing a compound of formula(IV) at its 4-position to give a compound of formula (VIII); reacting the compound of formula(VIII) with a compound of formula (V-1) or (V-2) to give a compound of formula(IX); and then chlorinating the compound of formula (IX) at its 4-position:

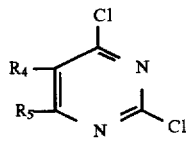
(IV)

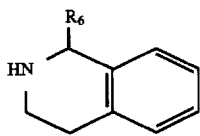
(V-1)

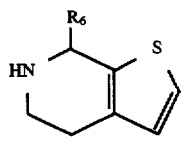
(V-2)

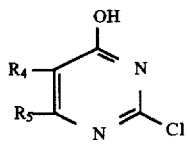
(VIII)

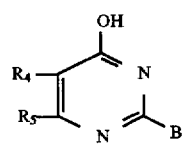
(IX)

wherein B, $R_4$, $R_5$ and $R_6$ are the same as defined in claim 1.

12. The process of claim 11, wherein the reaction of the compound of formula (VIII) with the compound of formula (V-1) or (V-2) is carried out in the presence of a solvent selected from the group consisting of dichloromethane, acetone, acetonitrile and dimethylformamide, and a base selected from the group consisting of triethylamine, N,N-dimethylaniline and pyridine.

13. A pharmaceutical composition comprising a therapeutically effective amount of any of the pyrimidine derivative compounds of claim 1 and a pharmaceutically acceptable carrier.

* * * * *